United States Patent
Shelton, IV et al.

(10) Patent No.: US 11,986,182 B2
(45) Date of Patent: May 21, 2024

(54) MULTI-POSITION RESTRAINING MEMBER FOR SLED MOVEMENT

(71) Applicant: Cilag GmbH International, Zug (CH)

(72) Inventors: Frederick E. Shelton, IV, Hillsboro, OH (US); Kevin M. Fiebig, Cincinnati, OH (US); Adam D. Hensel, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/402,732

(22) Filed: Aug. 16, 2021

(65) Prior Publication Data

US 2023/0045893 A1 Feb. 16, 2023

(51) Int. Cl.
*A61B 17/072* (2006.01)
*A61B 34/30* (2016.01)

(52) U.S. Cl.
CPC ........ *A61B 17/07207* (2013.01); *A61B 34/30* (2016.02); *A61B 2017/07271* (2013.01); *A61B 2017/07278* (2013.01)

(58) Field of Classification Search
CPC .............. A61B 17/07207; A61B 34/30; A61B 2017/07271; A61B 2017/07278
USPC .......... 227/176.1, 175.1–182.1; 606/75, 219, 606/220
See application file for complete search history.

(56) References Cited

U.S. PATENT DOCUMENTS

| | | | |
|---|---|---|---|
| 5,129,570 A | 7/1992 | Schulze et al. | |
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 7,810,692 B2 | 10/2010 | Hall et al. | |
| 7,832,408 B2 | 11/2010 | Shelton, IV et al. | |
| 7,845,537 B2 | 12/2010 | Shelton, IV et al. | |
| 8,083,120 B2 | 12/2011 | Shelton, IV et al. | |
| 8,210,411 B2 | 7/2012 | Yates et al. | |

(Continued)

FOREIGN PATENT DOCUMENTS

| EP | 2517639 A1 | 10/2012 |
|---|---|---|
| EP | 3417811 A2 | 12/2018 |

(Continued)

OTHER PUBLICATIONS

U.S. Appl. No. 17/402,674.

(Continued)

*Primary Examiner* — Dariush Seif
(74) *Attorney, Agent, or Firm* — Frost Brown Todd LLP

(57) ABSTRACT

A surgical instrument includes a body, a shaft assembly, an end effector, a stapling assembly, and a restriction feature. The shaft assembly extends distally from the body. The end effector being on a distal end of the shaft assembly and incudes a first second jaw. The stapling assembly is supported by one of the first jaw or the second jaw. The stapling assembly includes a wedge sled. The wedge sled is configured to move relative to the one of the first jaw or the second jaw to drive movement of one or more staples. The restriction feature is configured to releasably hold the wedge sled in a predetermined position within the stapling assembly while the stapling assembly is in a pre-fired configuration. At least a portion of the restriction feature is configured to respond to movement of the edge sled to release the restriction feature from the wedge sled.

20 Claims, 18 Drawing Sheets

(56) References Cited

U.S. PATENT DOCUMENTS

| | | |
|---|---|---|
| 8,408,439 B2 | 4/2013 | Huang et al. |
| 8,453,914 B2 | 6/2013 | Laurent et al. |
| 8,708,213 B2 | 4/2014 | Shelton, IV et al. |
| 9,060,770 B2 | 6/2015 | Shelton, IV et al. |
| 9,186,142 B2 | 11/2015 | Fanelli et al. |
| 9,517,065 B2 | 12/2016 | Simms et al. |
| 9,622,746 B2 | 4/2017 | Simms et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 9,839,487 B2 | 12/2017 | Dachs, II |
| 10,011,018 B2 | 7/2018 | McGrogan et al. |
| 10,092,292 B2 | 10/2018 | Boudreaux et al. |
| 10,307,170 B2 | 6/2019 | Parfett et al. |
| 10,485,621 B2 | 11/2019 | Morrissette et al. |
| 10,537,400 B2 | 1/2020 | Dachs, II et al. |
| 10,610,313 B2 | 4/2020 | Bailey et al. |
| 10,667,809 B2 | 6/2020 | Bakos et al. |
| 10,806,530 B2 | 10/2020 | Liao et al. |
| 10,863,988 B2 | 12/2020 | Patel et al. |
| 11,020,138 B2 | 6/2021 | Ragosta |
| 11,026,755 B2 | 6/2021 | Weir et al. |
| 11,076,926 B2 | 8/2021 | Ragosta et al. |
| 11,147,552 B2 | 10/2021 | Burbank et al. |
| 11,166,773 B2 | 11/2021 | Ragosta et al. |
| 11,234,700 B2 | 2/2022 | Ragosta et al. |
| 11,259,884 B2 | 3/2022 | Burbank |
| 11,395,656 B2* | 7/2022 | Aranyi ............. A61B 17/07207 |
| 11,406,377 B2* | 8/2022 | Schmid ............ A61B 17/07207 |
| 2006/0185682 A1 | 8/2006 | Marczyk |
| 2012/0209314 A1 | 8/2012 | Weir et al. |
| 2013/0146643 A1* | 6/2013 | Schmid ............... A61B 17/1155 |
| | | 227/176.1 |
| 2014/0166726 A1* | 6/2014 | Schellin .................. B29C 43/52 |
| | | 227/176.1 |
| 2014/0224686 A1* | 8/2014 | Aronhalt .............. A61B 17/068 |
| | | 206/339 |
| 2014/0263567 A1* | 9/2014 | Williams ......... A61B 17/07207 |
| | | 227/180.1 |
| 2014/0291378 A1* | 10/2014 | Shelton, IV ..... A61B 17/00234 |
| | | 227/175.2 |
| 2015/0297228 A1 | 10/2015 | Huitema et al. |
| 2016/0361126 A1 | 12/2016 | Schena et al. |
| 2017/0020617 A1 | 1/2017 | Weir et al. |
| 2017/0265865 A1 | 9/2017 | Burbank |
| 2017/0265954 A1 | 9/2017 | Burbank et al. |
| 2017/0296173 A1* | 10/2017 | Shelton, IV ......... A61B 17/068 |
| 2017/0333037 A1 | 11/2017 | Wellman et al. |
| 2018/0168592 A1* | 6/2018 | Overmyer ............. A61B 34/30 |
| 2018/0168646 A1* | 6/2018 | Shelton, IV ....... A61B 17/0682 |
| 2018/0168756 A1 | 6/2018 | Liao et al. |
| 2018/0271608 A1 | 9/2018 | Ragosta et al. |
| 2018/0310935 A1 | 11/2018 | Wixey |
| 2018/0325606 A1 | 11/2018 | Weir et al. |
| 2018/0344318 A1* | 12/2018 | Nicholas ............ A61B 1/00087 |
| 2018/0344419 A1 | 12/2018 | Dachs, II et al. |
| 2019/0038371 A1 | 2/2019 | Wixey et al. |
| 2019/0076142 A1 | 3/2019 | Wixey |
| 2019/0076143 A1 | 3/2019 | Smith |
| 2019/0167266 A1 | 6/2019 | Patel et al. |
| 2019/0200989 A1 | 7/2019 | Burbank et al. |
| 2019/0239967 A1 | 8/2019 | Ragosta et al. |
| 2019/0262088 A1 | 8/2019 | Burbank |
| 2019/0290281 A1* | 9/2019 | Aronhalt ............. A61B 17/072 |
| 2019/0298350 A1 | 10/2019 | Shelton, IV et al. |
| 2020/0015819 A1* | 1/2020 | Shelton, IV ......... A61B 17/072 |
| 2020/0138529 A1 | 5/2020 | Ragosta et al. |
| 2020/0246001 A1* | 8/2020 | Ming .................... A61B 17/105 |
| 2020/0261087 A1* | 8/2020 | Timm .................... A61B 90/06 |
| 2020/0397430 A1 | 12/2020 | Patel et al. |
| 2020/0405293 A1* | 12/2020 | Shelton, IV ..... A61B 17/07207 |
| 2020/0405301 A1 | 12/2020 | Shelton, IV et al. |
| 2021/0282770 A1* | 9/2021 | Fernandes ........ A61B 17/07207 |
| 2021/0307742 A1* | 10/2021 | Cappola ............. A61B 17/0686 |
| 2021/0393340 A1 | 12/2021 | Beckman et al. |
| 2021/0401433 A1 | 12/2021 | Freidel et al. |
| 2022/0167970 A1* | 6/2022 | Aronhalt ............ A61B 17/0686 |

FOREIGN PATENT DOCUMENTS

| | | |
|---|---|---|
| WO | WO 2015/153642 A1 | 10/2015 |
| WO | WO 2017/083125 A1 | 5/2017 |
| WO | WO 2017/083129 A1 | 5/2017 |
| WO | WO 2018/049198 A1 | 3/2018 |
| WO | WO 2018/049206 A1 | 3/2018 |
| WO | WO 2018/049211 A1 | 3/2018 |
| WO | WO 2018/049217 A1 | 3/2018 |
| WO | WO 2018/052806 A1 | 3/2018 |
| WO | WO 2018/052810 A1 | 3/2018 |
| WO | WO 2018/071497 A1 | 4/2018 |
| WO | WO 2018/071763 A1 | 4/2018 |
| WO | WO 2018/085529 A2 | 5/2018 |
| WO | WO 2018/175467 A1 | 9/2018 |
| WO | WO 2019/165403 A1 | 8/2019 |
| WO | WO 2020/131290 A1 | 6/2020 |

OTHER PUBLICATIONS

U.S. Appl. No. 17/402,675.
U.S. Appl. No. 17/402,677.
U.S. Appl. No. 17/402,679.
U.S. Appl. No. 17/402,695.
U.S. Appl. No. 17/402,701.
U.S. Appl. No. 17/402,703.
U.S. Appl. No. 17/402,720.
U.S. Appl. No. 17/402,738.
U.S. Appl. No. 17/402,744.
U.S. Appl. No. 17/402,749.
U.S. Appl. No. 17/402,759.
U.S. Appl. No. 17/088,941, entitled "Surgical Stapler End Effector Sled Having Cartridge Wall Support Feature," filed Nov. 4, 2020.
U.S. Appl. No. 17/402,674, entitled "Methods of Operating a Robotic Surgical Stapler," filed Aug. 16, 2021.
U.S. Appl. No. 17/402,675, entitled "Multi-Threshold Motor Control Algorithm for Powered Surgical Stapler," filed Aug. 16, 2021.
U.S. Appl. No. 17/402,677, entitled "Variable Response Motor Control Algorithm for Powered Surgical Stapler," filed Aug. 16, 2021.
U.S. Appl. No. 17/402,679, entitled "Powered Surgical Stapler Having Independently Operable Closure and Firing Systems," filed Aug. 16, 2021.
U.S. Appl. No. 17/402,695, entitled "Firing System Features for Surgical Stapler," filed Aug. 16, 2021.
U.S. Appl. No. 17/402,701, entitled "Multiple-Sensor Firing Lockout Mechanism for Powered Surgical Stapler," filed Aug. 16, 2021.
U.S. Appl. No. 17/402,703, entitled "Proximally Located Firing Lockout Mechanism for Surgical Stapler," filed Aug. 16, 2021.
U.S. Appl. No. 17/402,720, entitled "Cartridge-Based Firing Lockout Mechanism for Surgical Stapler," filed Aug. 16, 2021.
U.S. Appl. No. 17/402,738, entitled "Firing Member Tracking Feature for Surgical Stapler," filed Aug. 16, 2021.
U.S. Appl. No. 17/402,744, entitled "Adjustable Power Transmission Mechanism for Powered Surgical Stapler," filed Aug. 16, 2021.
U.S. Appl. No. 17/402,749, entitled "Firing Bailout System for Powered Surgical Stapler," filed Aug. 16, 2021.
U.S. Appl. No. 17/402,759, entitled "Deflectable Firing Member for Surgical Stapler," filed Aug. 16, 2021.
U.S. Pat. Pub. No. 2023/0045998.
U.S. Pat. Pub. No. 2023/0048444.
U.S. Pat. Pub. No. 2023/0049736.
U.S. Pat. Pub. No. 2023/0050358.
U.S. Pat. Pub. No. 2023/0050707.
U.S. Pat. Pub. No. 2023/0051105.
U.S. Pat. Pub. No. 2023/0051222.
U.S. Pat. Pub. No. 2023/0051271.
U.S. Pat. Pub. No. 2023/0051361.
U.S. Pat. Pub. No. 2023/0051756.
U.S. Pat. Pub. No. 2023/0051938.

(56) References Cited

OTHER PUBLICATIONS

U.S. Pat. Pub. No. 2023/0052307.
International Search Report and Written Opinion dated Jan. 23, 2023, for International Application No. PCT/IB2022/057618, 19 pages.

* cited by examiner

MULTI-POSITION RESTRAINING MEMBER FOR SLED MOVEMENT

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically surgical systems. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a surgical stapler, a tissue grasper, a needle driver, an electrosurgical cautery probe, etc. Each of these structures performs functions for the surgeon, for example, cutting tissue, coagulating tissue, holding or driving a needle, grasping a blood vessel, dissecting tissue, or cauterizing tissue.

Examples of surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers and associated features are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued on Nov. 17, 2015; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 10,092,292, entitled "Staple Forming Features for Surgical Stapling Instrument," issued Oct. 9, 2018; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; and U.S. Pat. No. 8,210,411, entitled "Motor-Driven Surgical Instrument," issued Jul. 3, 2012. The disclosure of each of the above-cited U.S. Patents is incorporated by reference herein in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
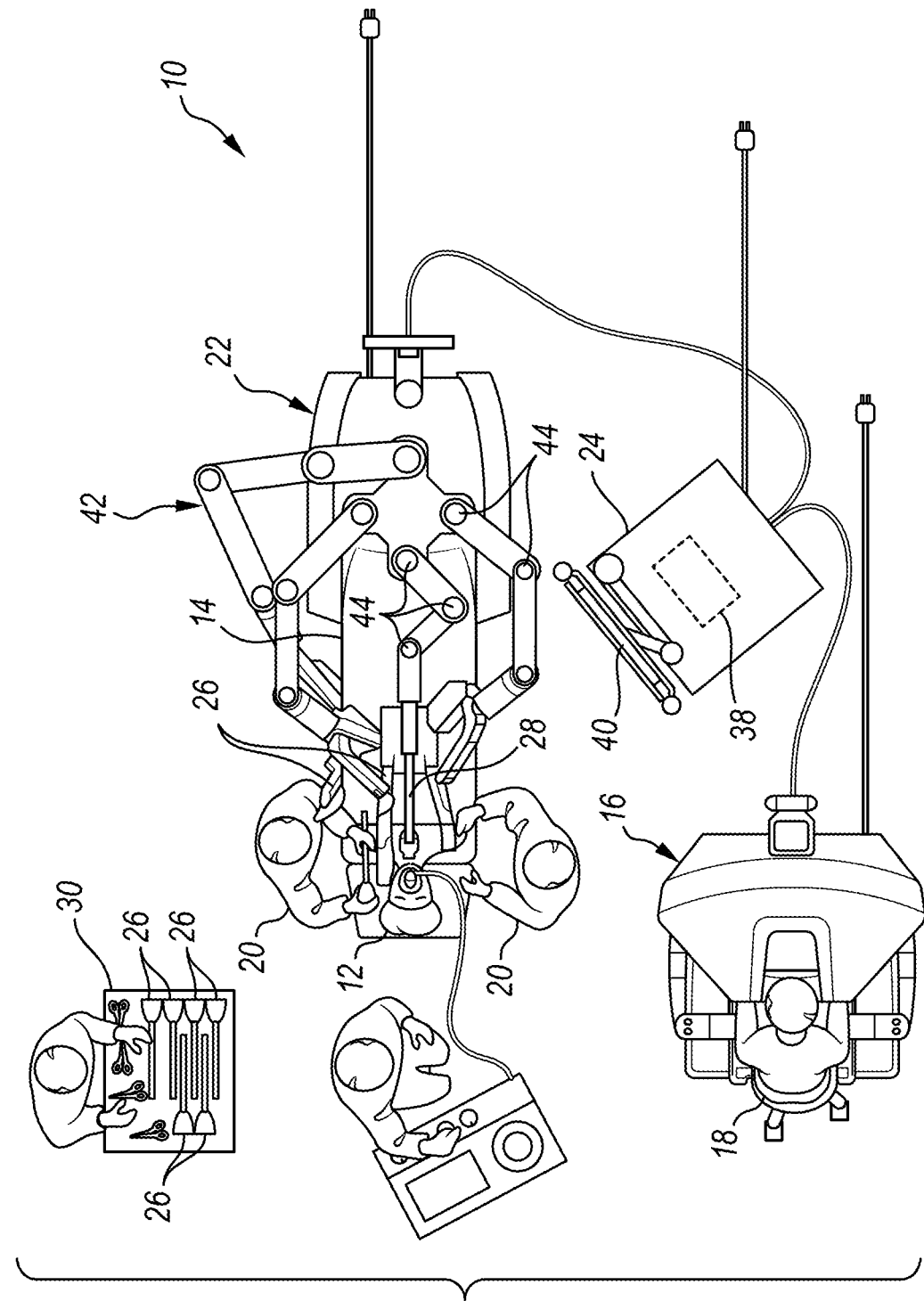
FIG. 1 depicts a top plan view of a robotic surgical system being used to perform a surgical procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "clockwise," "counterclockwise," "inner," "outer," "upper," "lower," and the like also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

I. Exemplary Robotic Surgical System

A. Overview

FIG. 1 shows a top plan view of an exemplary robotic surgical system (10) that may be used for performing a diagnostic or surgical procedure on a patient (12) who is lying down on an operating table (14). Robotic surgical system (10) may be constructed and operable in accordance with at least some of the teachings of U.S. Pat. No. 9,839,487, entitled "Backup Latch Release for Surgical Instrument," issued Dec. 12, 2017; U.S. Pat. No. 10,485,621, entitled "Sterile Barrier Between Surgical Instrument and Teleoperated Actuator," issued Nov. 26, 2019; U.S. Pat. No. 10,806,530, entitled "System and Method for Patient-Side Instrument Control," issued Oct. 20, 2020; U.S. Pat. No. 10,537,400, entitled "Detection Pins to Determine Presence of Surgical Instrument and Adapter on Manipulator," issued Jan. 21, 2020; U.S. Pat. No. 10,863,988, entitled "Surgical Instrument with Lockout Mechanism," published Dec. 15, 2020; U.S. Pat. No. 10,610,313, entitled "Surgical Instrument with Shiftable Transmission," issued Apr. 7, 2020; U.S. Pub. No. 2018/0271608, entitled "Manual Release for Medical Device Drive System," published Sep. 27, 2018; U.S. Pub. No. 2018/0325606, entitled "Systems and Methods for Operating an End Effector," published Nov. 15, 2018; U.S. Pub. No. 2019/0200989, entitled "Stapler Reload Detection and Identification," published Jul. 4, 2019; U.S. Pub. No. 2019/0239967, entitled "Stapler Beam Architecture," published Aug. 8, 2019; U.S. Pub. No. 2019/0262088, entitled "Robotic Surgical Stapler Assembly Configured to Use Stapler Reload," published Aug. 29, 2019; U.S. Pub. No. 2019/0239877, entitled "Wrist Architecture," published Aug. 8, 2019; U.S. Pub. No. 2019/0201150, entitled "Push-Pull Surgical Instrument End Effector Actuation Using Flexible Tension Member," published Jul. 4, 2019; U.S. Pub. No. 2019/0282233, entitled "Stapler Cartridge With an Integral Knife," published Sep. 19, 2019; U.S. Pub. No. 2019/0262088, entitled "Robotic Surgical Stapler Assembly Configured to Use Stapler Reload," published Aug. 29, 2019;

U.S. Pub. No. 2020/0138529, entitled "Locking System for Medical Device Drive System," published May 7, 2020; and/or U.S. Pub. No. 2020/0397430, entitled "Surgical Instrument With Lockout Mechanism," published Dec. 24, 2020. The disclosure of each of the above-cited U.S. Patents and U.S. Patent Publications is incorporated by reference herein in its entirety.

Robotic surgical system (10) may include a surgeon's console (16) for use by a surgeon (18) during a surgical procedure. One or more assistants (20) may also participate in the procedure. Robotic surgical system (10) may include a patient side cart (22) (i.e., a surgical robot) and an electronics cart (24). Patient side cart (22) may manipulate at least one surgical instrument (26) (also referred to as a "tool assembly" or "tool") through an incision in the body of patient (12) while surgeon (18) views the surgical site through surgeon's console (16). As will be described in greater detail below, surgical instrument(s) (26) and an imaging device (shown as an endoscope (28)) may be removably coupled with patient side cart (22). Electronics cart (24) may be used to process the images of the surgical site for subsequent display to the surgeon (18) through surgeon's console (16). Electronics cart (24) may be coupled with endoscope (28) and may include a processor (38) (shown schematically) to process captured images for subsequent display, such as to surgeon (18) on the surgeon's console (16), on a display (40) of electronics cart (24), or another suitable display located locally and/or remotely. The images may also be processed by a combination of electronics cart (24) and processor (38), which may be coupled together to process the captured images jointly, sequentially, and/or combinations thereof. Electronics cart (24) may overlay the captured images with a virtual control interface prior to displaying combined images to the surgeon (18) via surgeon's console (16).

Figure 2:
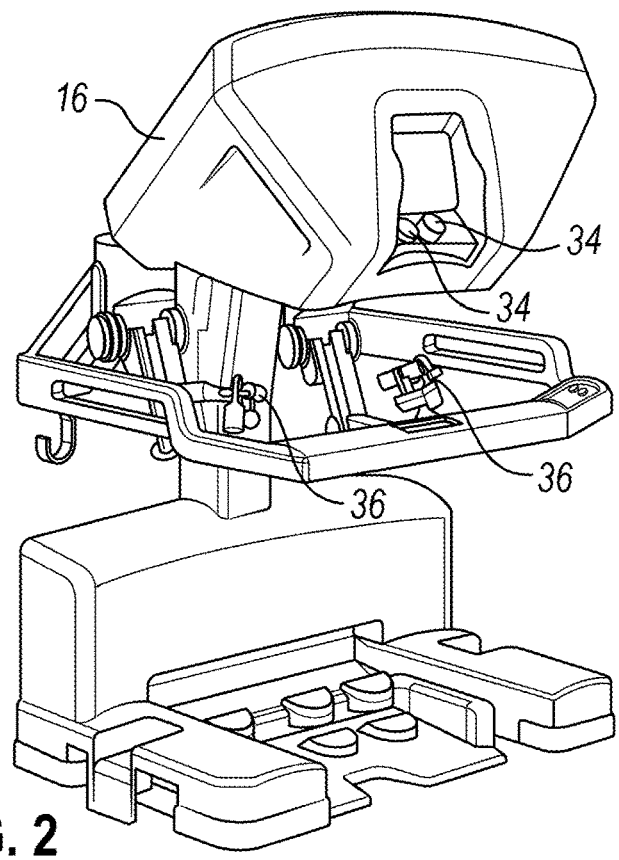
FIG. 2 depicts a perspective view of a surgeon's control console of the robotic surgical system of FIG. 1.

FIG. 2 shows a perspective view of surgeon's console (16). Surgeon's console (16) includes a left eye display (32) and a right eye display (34) for presenting surgeon (18) with a coordinated stereo view of the surgical site that enables depth perception. Surgeon's console (16) includes one or more input control devices (36) causing patient side cart (22) (shown in FIG. 1) to manipulate one or more surgical instruments (26). Input control devices (36) may provide the same degrees of freedom as their associated surgical instruments (26) (shown in FIG. 1) to provide surgeon (18) with telepresence, or the perception that the input control devices (36) are integral with surgical instruments (26). To this end, position, force, and tactile feedback sensors (not shown) may be employed to transmit position, force, and tactile sensations from surgical instruments (26) back to the surgeon's hands through input control devices (36). In some instances, surgeon's console (16) may be located in the same room as the patient so that surgeon (18) may directly monitor the procedure, be physically present if necessary, and speak to an assistant directly rather than over the telephone or other communication medium. Alternatively, surgeon (18) may be located in a different room, a completely different building, or other remote location from the patient allowing for remote surgical procedures.

Figure 3:
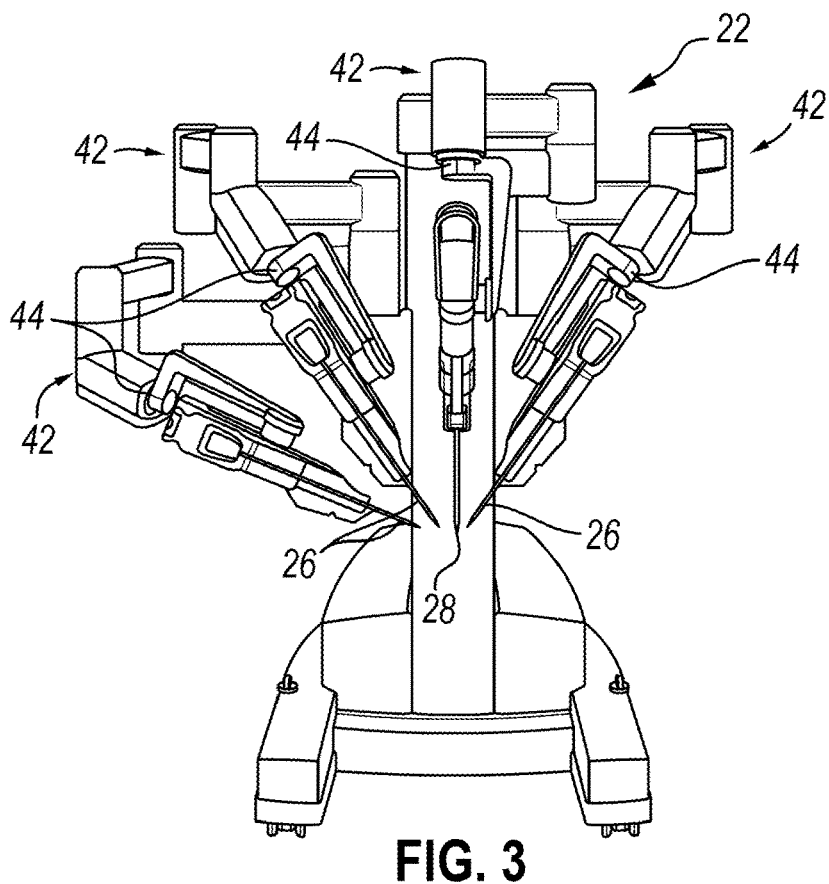
FIG. 3 depicts a front elevation view of a patient side cart of the robotic surgical system of FIG. 1.

FIG. 3 shows patient side cart (22) that manipulates surgical instruments (26). An image of the surgical site may be obtained by endoscope (28), which may include a stereoscopic endoscope. Manipulation is provided by robotic mechanisms, shown as robotic arms (42) that include at least one robotic joint (44) and an output coupler (not shown) that is configured to removable secure surgical instrument (26) with robotic arm (42). Endoscope (28) and surgical tools (26) may be positioned and manipulated through incisions in the patient so that a kinematic remote center is maintained at the incision to minimize the size of the incision. Images of the surgical site may include images of the distal ends of the surgical instruments (26) when they are positioned within the field-of-view of the endoscope (28). Patient side cart (22) may output the captured images for processing outside electronics cart (24). The number of surgical instruments (26) used at one time will generally depend on the diagnostic or surgical procedure and the space constraints within the operating room, among other factors. To change one or more of surgical instruments (26) being used during a procedure, assistant(s) (20) may remove surgical instrument (26) from patient side cart (22) and replace surgical instrument (26) with another surgical instrument (26) from a tray (30) (shown in FIG. 1) in the operating room.

B. Exemplary Surgical Instrument

Figure 4:
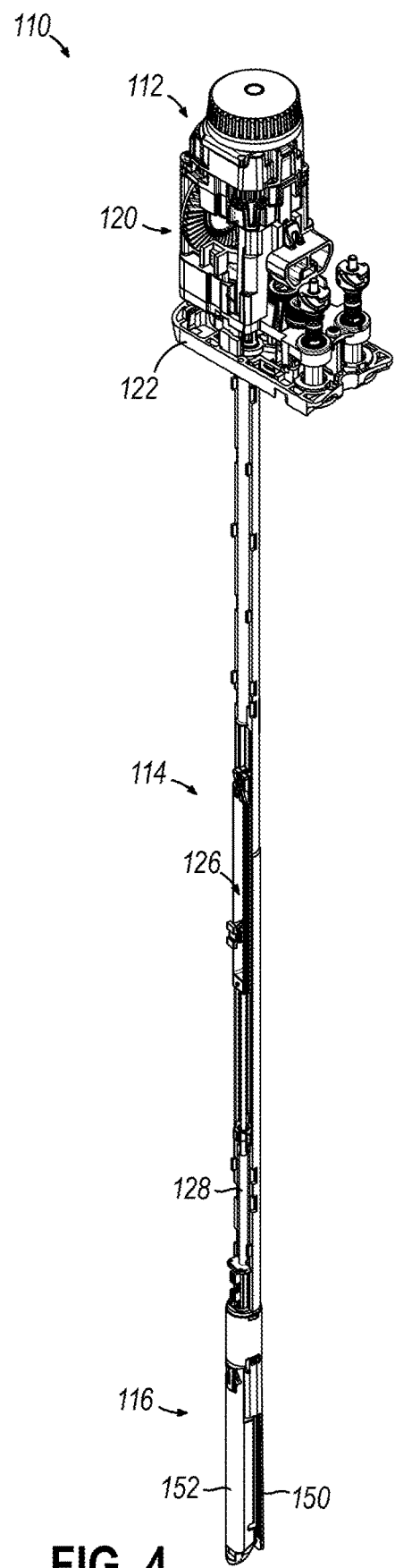
FIG. 4 depicts a perspective view of an exemplary surgical instrument that may be used with the robotic surgical system of FIG. 1, where the surgical instrument includes an instrument base, an elongate shaft, and an end effector, with select portions of the surgical instrument omitted to reveal internal features.
Figure 5:
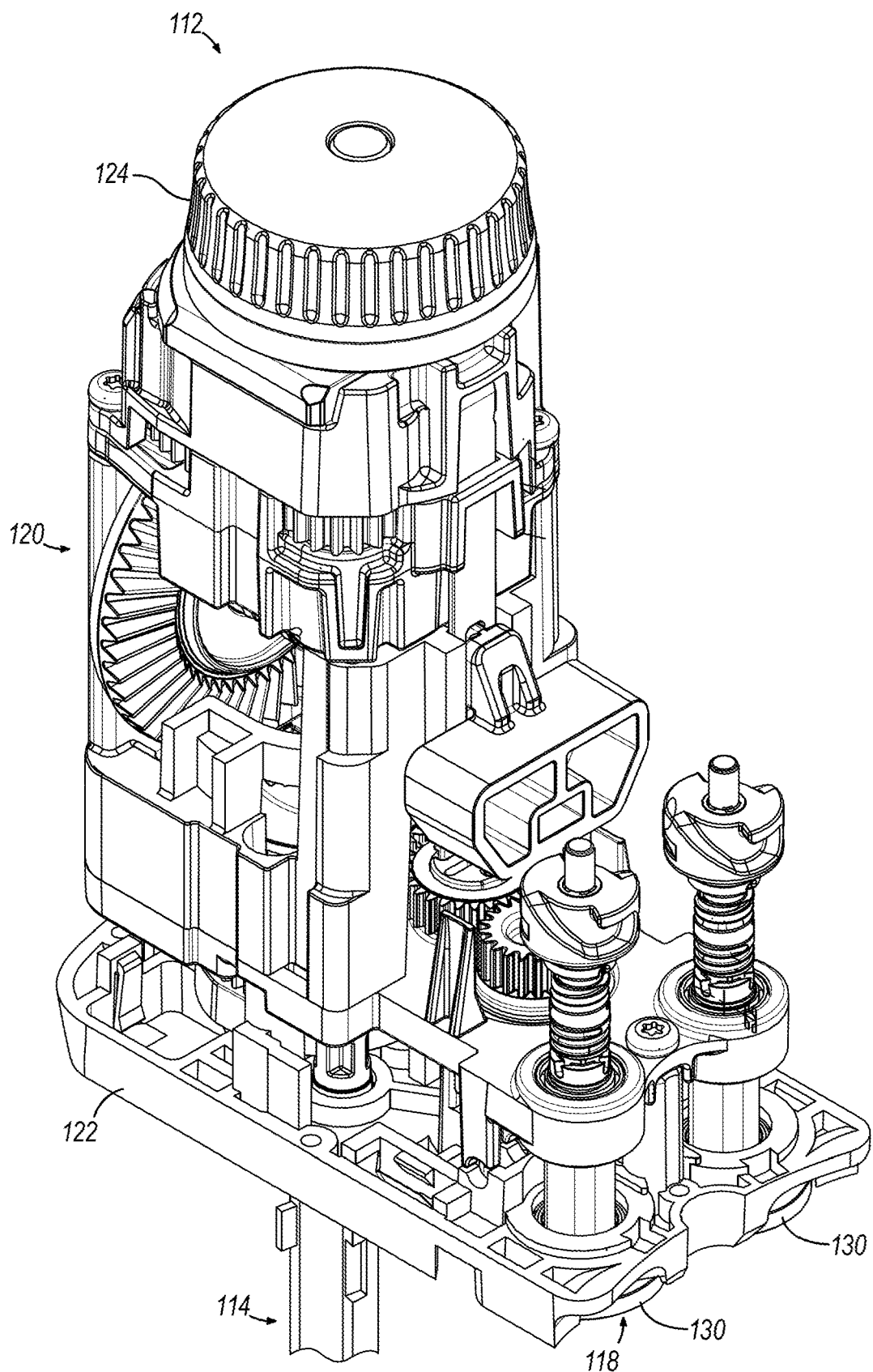
FIG. 5 depicts an enlarged perspective view of the instrument base of the surgical instrument of FIG. 4, with an outer housing omitted to reveal internal features.

FIGS. 4-5 show an exemplary surgical instrument (110) that may be mounted on and used with patient side cart (22) shown in FIG. 3. Surgical instrument (110) can have any of a variety of configurations capable of performing one or more surgical functions. As shown, surgical instrument (110) includes an instrument base (112), a shaft assembly (114) extending distally from instrument base (112), and an end effector (116) at a distal end of shaft assembly (114). Instrument base (112) includes an attachment interface (118) that includes input couplers (130) that are configured to interface with and be driven by corresponding output couplers (not shown) of robotic arm (42) of patient side cart (22).

FIG. 5 shows an enlarged perspective view of instrument base (112) of surgical instrument (110). Instrument base (112) includes a drive system (120) mounted on a chassis (122) and having one or more actuators for actuating end effector (116) to clamp, staple, and cut tissue, and for articulating end effector (116) relative to a longitudinal axis defined by shaft assembly (114). Drive system (120) may include a manual actuator (124), which is shown in the form of a knob configured to be manually rotated. Manual actuator (124) may engage other components of surgical instrument (110) to serve as a "bailout" mechanism to obtain a desired movement in end effector (116) without powered actuation of drive system (120). Shaft assembly (114) may include additional drive components, such as portions of a drive train (126), that may couple instrument base (112) to a moveable feature (128) of shaft assembly (114) that may be coupled to end effector (116). Shaft assembly (114) may be configured for use with a variety of interchangeable end effectors (116), such as a cutter, grasper, a cautery tool, a camera, a light, or a surgical stapler, for example.

C. First Exemplary End Effector

Figure 6:
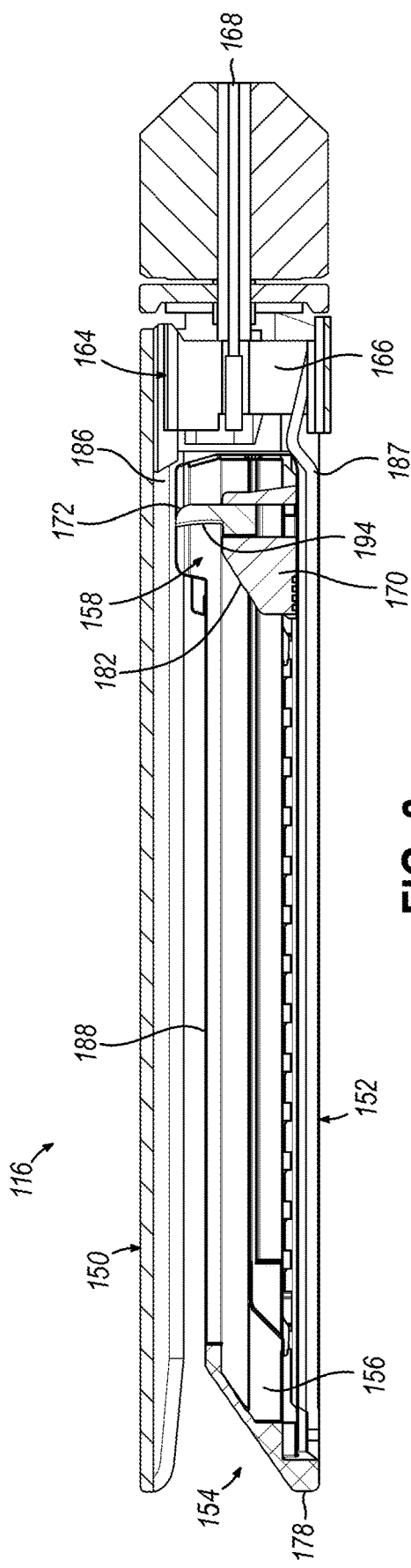
FIG. 6 depicts a side cross-sectional view of the end effector of FIG. 4, where the end effector includes a staple cartridge.

FIG. 6 shows a cross-sectional side view of end effector (116) of surgical instrument (110). End effector (116) extends distally from a distal end of shaft assembly (114). In the present example, end effector (116) comprises a surgical stapler, which may also be referred to herein as an "endocutter," configured to clamp, cut, and staple tissue. As illustrated, end effector (116) includes opposing upper and lower jaws (150, 152) configured to move relative to one another between open and closed positions for clamping and releasing tissue.

One or both of upper and lower jaws (150, 152) may be configured to pivot and thereby actuate end effector (116) between open and closed positions. Lower jaw (152) includes a removable staple cartridge (154). In the illustrated example, lower jaw (152) is pivotable relative to upper jaw (150) to move between an open, unclamped position and a closed, clamped position. In other examples, upper jaw (150) may move relative to lower jaw (152) (e.g., similar to end effector (210) of FIGS. 9-10). In still other examples, both and upper and lower jaws (150, 152) may move to actuate end effector (116) between open and closed positions. In the present example, lower jaw (152) is referred to as a "cartridge jaw" or "channel jaw," and upper jaw (150) is referred to as an "anvil jaw."

Figure 8:
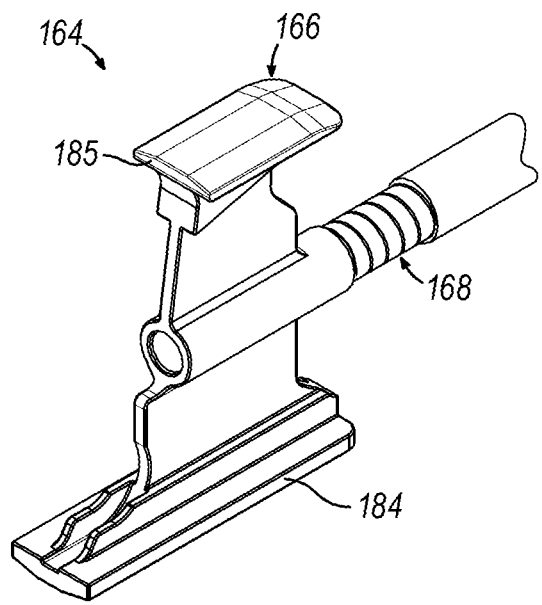
FIG. 8 depicts a driving assembly configured for use with the staple cartridge of FIG. 7.
Figure 9:
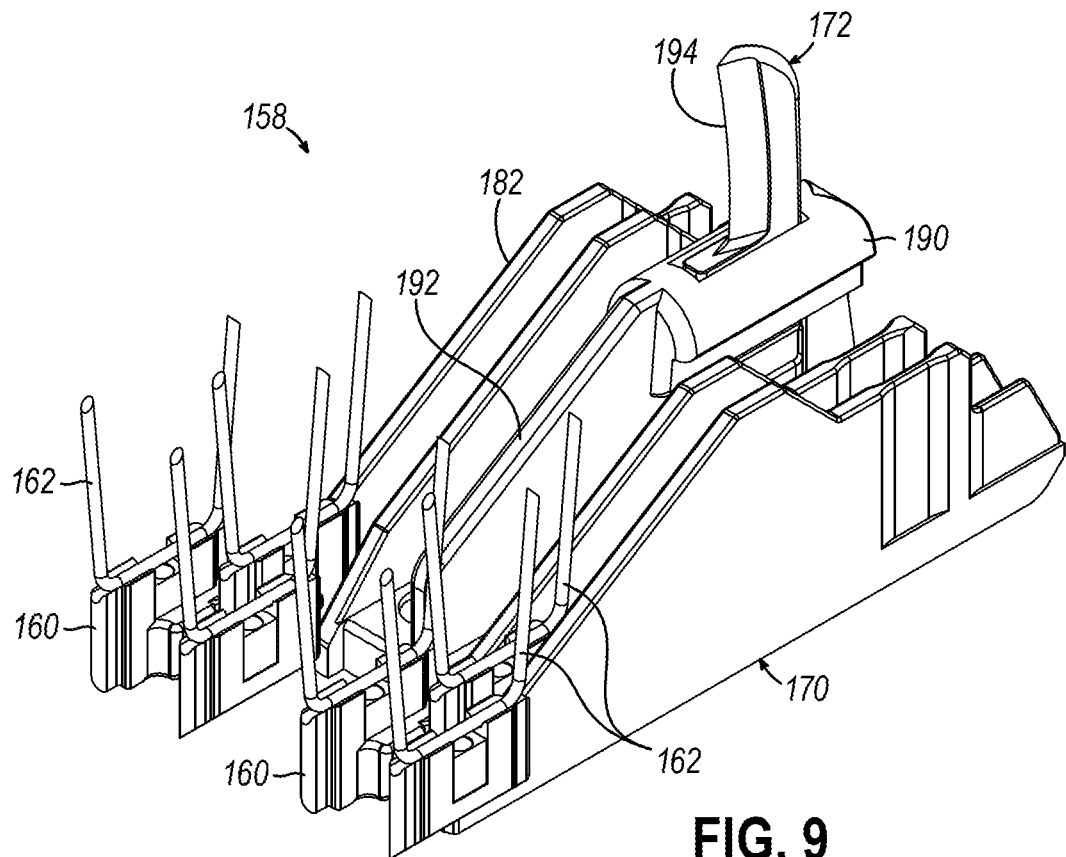
FIG. 9 depicts a firing assembly, staple drivers, and staples configured for use with the staple cartridge of FIG. 7.

Upper jaw (150) defines a surface that has a plurality of pockets (not shown) and operates as an anvil to deform staples ejected from staple cartridge (154) during operation. Staple cartridge (154) is replaceable, for example, by removing a used staple cartridge (154) from end effector (116) and inserting a new staple cartridge (154) into lower jaw (152). Staple cartridge (154) includes a staple cartridge body (156) that houses a firing assembly (158), a plurality of staple drivers (160) (also referred to as staple pushers), and a plurality of staples (162). As shown in FIGS. 6 and 8, end effector (116) includes a driving assembly (164) that includes a pusher member (166) that is operatively coupled with an actuation mechanism via a push rod (168). As shown in FIG. 6 and FIG. 9, firing assembly (158) includes a wedge sled (170) (also referred to as a staple pushing shuttle), and a knife member (172).

Figure 7:
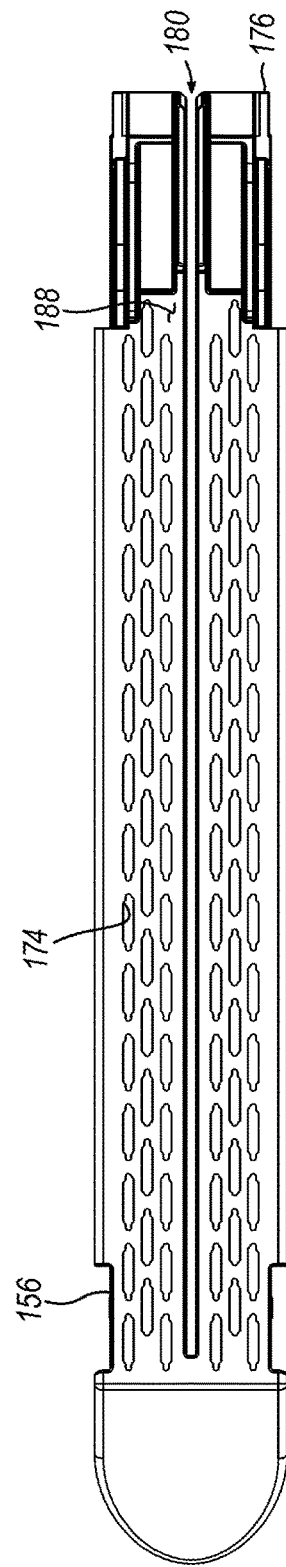
FIG. 7 depicts a top view of a deck of the staple cartridge of FIG. 6.

FIG. 7 shows a top view of staple cartridge body (156). Staple cartridge body (156) includes an array of staple accommodating apertures (174) (also known as "openings") extending through an upper deck (188) of staple cartridge body (156). Each aperture (174) slidably houses a respective staple (162) in an unformed state and a free end of a corresponding staple driver (160) positioned beneath the unformed staple (162). Staple cartridge (154) includes proximal and distal ends (176, 178). In operation, staples (162) are sequentially deployed from apertures (174) by staple drivers (160) starting at proximal end (176) and advancing toward distal end (178). A vertical slot (180), configured to accommodate knife member (172), extends through part of staple cartridge (154).

FIG. 8 shows pusher member (166) as including first and second flanges (184, 185). First flange (184) is configured to be received in a longitudinal slot (186) (shown in FIG. 6) of upper jaw (150) and second flange (185) is configured to be received in a longitudinal slot (187) (shown in FIG. 6) of staple cartridge body (156) of lower jaw (152). First and second flanges (184, 185) move along longitudinal slots (186, 187) during actuation of pusher member (166). In some versions, pusher member (166) may include a single flange (e.g., omitting first flange (184)). As shown, longitudinal slot (186) is generally enclosed and longitudinal slot (187) opens to an exterior surface of lower jaw (152).

FIG. 9 shows a perspective view of firing assembly (158), which is configured to be slidably received within the proximal end of staple cartridge body (156) in a longitudinal direction prior to engaging staple drivers (160) and staples (162). Wedge sled (170) of firing assembly (158) slidingly interfaces with staple cartridge body (156). More specifically, wedge sled (170) advances distally along staple cartridge body (156) such that ramp portions (182) of wedge sled (170) contact staple drivers (160). Staple drivers (160) push staples (162) out of apertures (174) of staple cartridge body (156) to penetrate through and staple tissue clamped between staple cartridge body (156) and upper jaw (150). An initial distal actuation of pusher member (166) may move pusher member (166) into contact with wedge sled (170), with further actuation pushing staples (162) transversely out of staple cartridge body (156).

At an initial proximal position of wedge sled (170), knife member (172) is housed within staple cartridge body (156). The position of knife member (172) is controlled during a first portion of the movement of wedge sled (170) from proximal end (176) of staple cartridge body (156) to distal end (178) of staple cartridge (154), so that a cutting edge (194) of knife member (172) extends through vertical slot (180). Vertical slot (180) accommodates cutting edge (194) of knife member (172) as firing assembly (158) is moved toward distal end (178) of staple cartridge (154). Wedge sled (170) includes a guide member (190) that provides a bearing surface that cooperates with a similarly shaped surface of staple cartridge body (156) to guide wedge sled (170). Guide member (190) extends from a vertical rib member (192) of wedge sled (170), which forms a central portion of wedge sled (170). In some versions, knife member (172), or at least cutting edge (194), may be retracted below upper deck (188) of staple cartridge body (156) prior to firing assembly (158) reaching its distal most position adjacent to distal end (178) of staple cartridge (154).

D. Second Exemplary End Effector

Figure 10:
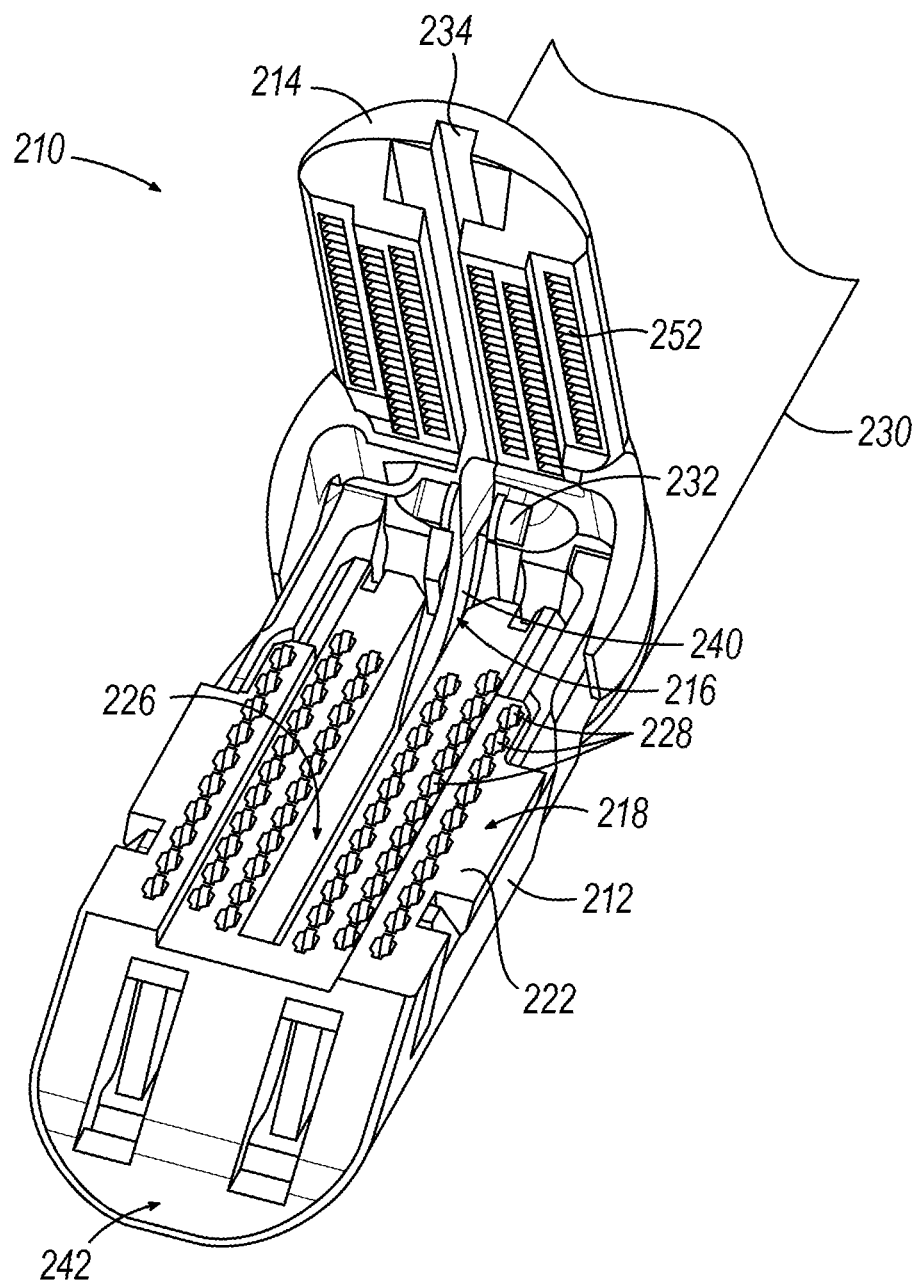
FIG. 10 depicts a second exemplary end effector that may be configured for use with the robotic surgical system of FIG. 1.
Figure 11:
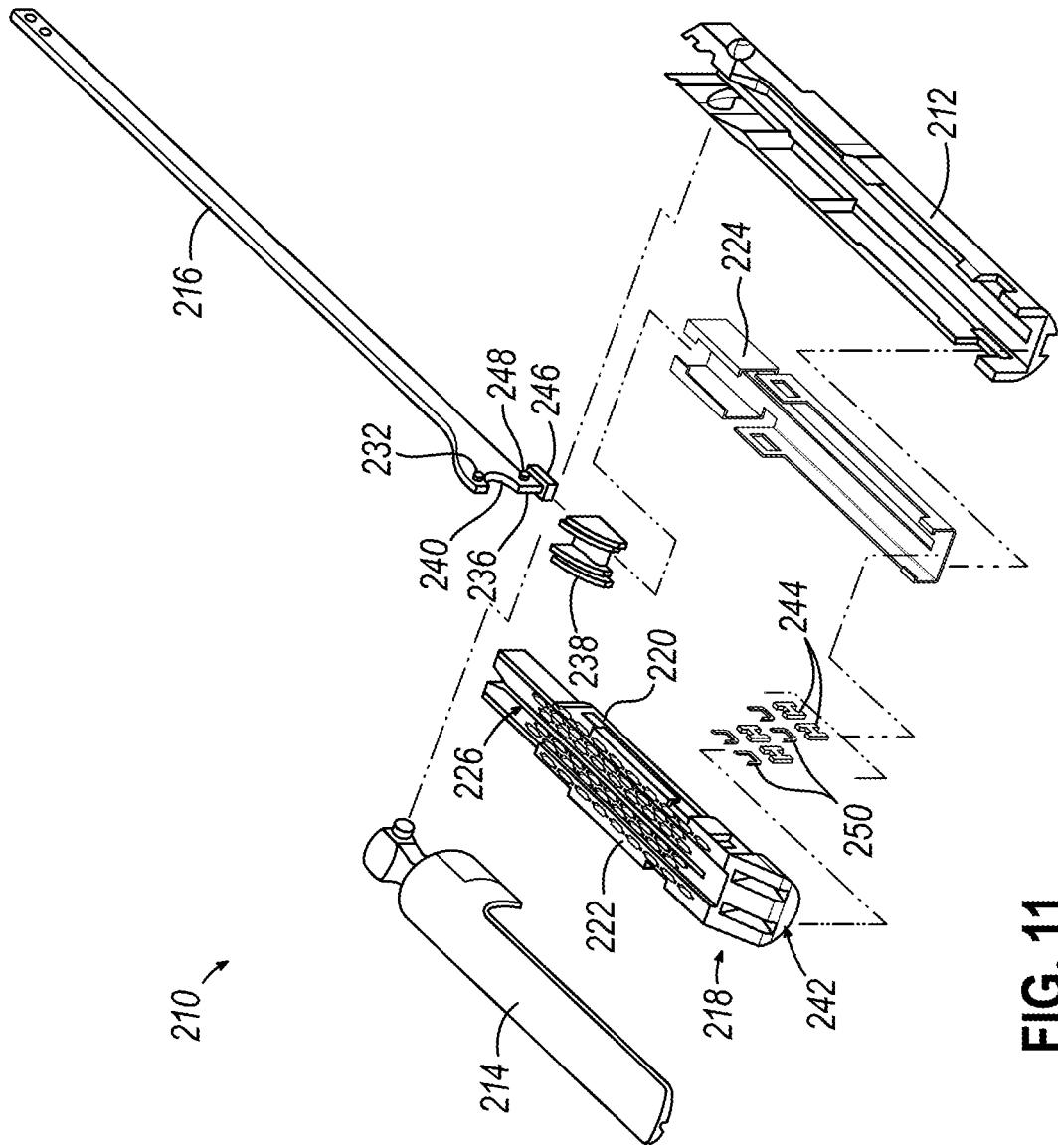
FIG. 11 depicts an exploded view of the end effector of FIG. 10.

FIGS. 10-11 show a second exemplary end effector (210), in an open position, that is configured to compress, cut, and staple tissue. End effector (210) may be configured for use with surgical instrument (110) of FIG. 4, or with surgical instruments of alternative constructions. End effector (210) may be constructed and operable in accordance with at least some of the teachings of U.S. patent application Ser. No. 16/916,295, entitled "Surgical Stapler Cartridge Retainer with Ejector Feature," filed Aug. 3, 2020, issued as U.S. Pat. No. 11,744,544 on Sep. 5, 2023, the disclosure of which is incorporated by reference herein in its entirety. End effector (210) of the present example includes a lower jaw (212) and an upper jaw in the form of a pivotable anvil (214). Lower jaw (212) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (214) may be constructed and operable in accordance with at least some of the teachings of U.S. Pat. No. 10,092,292, entitled "Staple Forming Features for Surgical Stapling Instrument," issued Oct. 9, 2018, the disclosure of which is incorporated by reference herein in its entirety.

FIG. 10 shows end effector (210), where anvil (214) is pivoted to an open position and a firing beam (216) is proximally positioned, allowing an unspent staple cartridge (218) to be removably installed into a channel of lower jaw (212). Staple cartridge (218) includes a cartridge body (220), which presents an upper deck (222) and is coupled with a lower cartridge tray (224). A vertical slot (226) is formed through part of staple cartridge (218) and opens upwardly through upper deck (222). One or more rows of staple apertures (228) are formed through upper deck (222) on one side of vertical slot (226), with one or more rows of staple apertures (228) being formed through upper deck (222) on the other side of vertical slot (226). End effector (210) is closed by distally advancing a closure tube (not shown) and a closure ring (230). Firing beam (216) is then advanced distally so that an upper pin of firing beam (216) enters longitudinal anvil slot (234). Simultaneously, a pusher block (236) located at the distal end of firing beam (216) engages a wedge sled (238) housed within cartridge body (220), such that wedge sled (238) is pushed distally by pusher block (236) as firing beam (216) is advanced distally through staple cartridge (218) and anvil (214).

During firing, cutting edge (240) of firing beam (216) enters vertical slot (226) toward distal end (242) of staple cartridge (218), severing tissue clamped between staple cartridge (218) and anvil (214). As best seen in FIG. 11, wedge sled (238) presents inclined cam surfaces that urge staple drivers (244) upwardly as wedge sled (238) is driven distally through staple cartridge (218). A firing beam cap (246) slidably engages a lower surface of lower jaw (212). Wedge sled (238) is movable longitudinally within staple cartridge (218), while staple drivers (244) are movable vertically within staple cartridge (218). A middle pin (248) and pusher block (236) of firing beam (216) together actuate staple cartridge (218) by entering into vertical slot (226) within staple cartridge (218), driving wedge sled (238) distally into upward camming contact with staple drivers (244) that in turn drive staples (250) out through staple apertures (228) and into forming contact with staple forming pockets (252) on the inner surface of anvil (214). Additional examples of alternative surgical instruments and/or associated features are described in U.S. patent application Ser. No. 16/946,363, entitled "Articulation Mechanisms for Robotic Surgical Tools," filed on Jun. 18, 2020, issued as U.S. Pat. No. 11,896,202 on Feb. 13, 2024, the disclosure of which is hereby incorporated by reference herein in its entirety.

It will be appreciated that any one or more of the teachings described below may be combined with any one or more of the teachings described above in connection with FIGS. 1-11.

II. Exemplary Alternative Staple Cartridges with Sled Restriction Features

In some examples, structures similar to wedge sled (170) may include sharp tissue cutting features similar to knife member (172) and/or cutting edge (194). Incorporation of such sharp features into structures similar to wedge sled (170) may be desirable in some circumstances to, for example, promote tissue cutting in a relatively tight sequence with stapling. However, in other examples, it may be desirable to incorporate such sharp features into other components like firing beam (216) discussed above. Such a configuration may be desirable to avoid premature engagement between sharp features and other surfaces such as tissue, tubes, sutures, or ancillary clinical equipment. Thus, in some contexts it may be desirable to incorporate features into structures similar to staple cartridge (154) to provide additional control over structures similar to wedge sled (170) to obtain the benefits of incorporating certain sharp features into structures similar to wedge sled (170) while also retaining the benefits associated with such sharp features being incorporated into other alternative structures.

Although various embodiments are described herein as including additional control structures, it should be understood that in other examples other alternative features may be added to the embodiments described herein without departing from the concepts described herein. Additionally, some specific features of the embodiments described herein may be combined with other specific features of other embodiments also without departing from the concepts described herein. Various suitable combinations of features will be apparent to those skilled in the art in view of the teachings herein.

Figure 12:
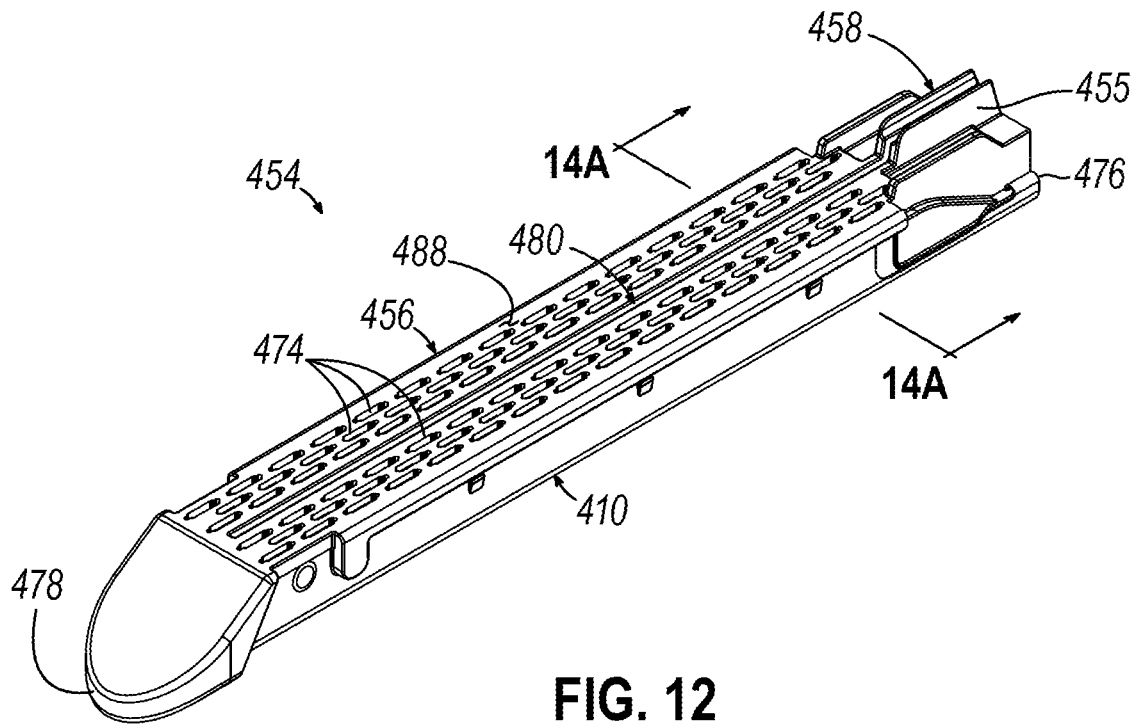
FIG. 12 depicts a perspective view of an exemplary alternative staple cartridge for use with the surgical instrument of FIG. 4.

A. Exemplary Alternative Staple Cartridge with Pan having Restriction Feature FIG. 12 shows an exemplary alternative staple cartridge (454) that may be readily used with end effector (116, 210) described above in lieu of staple cartridges (154, 254). Staple cartridge (454) is substantially similar to staple cartridge (154) described above, unless where otherwise noted herein. For instance, like with staple cartridge (154), staple cartridge (454) of the present example includes a staple cartridge body (456) that is configured to house a firing assembly (458), a plurality of staple drivers (not shown), and a plurality of staples (not shown). As with firing assembly (158) described above, firing assembly (458) of the present example includes a wedge sled (470) and a knife member (472) (see FIG. 14A).

Staple cartridge body (456) of the present example is similar to staple cartridge body (156) in that staple cartridge body (456) includes an array of staple accommodating apertures (474) extending through an upper deck (488) of staple cartridge body (456). Staple cartridge (454) includes proximal and distal ends (476, 478). In operation, staples (not shown) are sequentially deployed starting at proximal end (476) by advancing wedge sled (470) toward distal end (478). A vertical slot (480) configured to accommodate knife member (472) through part of staple cartridge (454) to permit a cutting edge (494) to cut tissue as the staples are driven via wedge sled (470).

Staple cartridge (454) further includes a blade guard (455) (also referred to as a cover, sheath, and/or compartment). Blade guard (455) extends upwardly from upper deck (488) and is disposed at a proximal end of cartridge body (456). In the present example, blade guard (455) is defined by two upwardly extending slats disposed on each side of vertical slot (480). As will be understood, blade guard (455) is configured to contain knife member (472) to avoid inadvertent contact with cutting edge (494) when staple cartridge (454) is not in use. As such, the particular position of blade guard (455) relative to cartridge body (456) corresponds to a proximal or home position of wedge sled (470).

Figure 13:
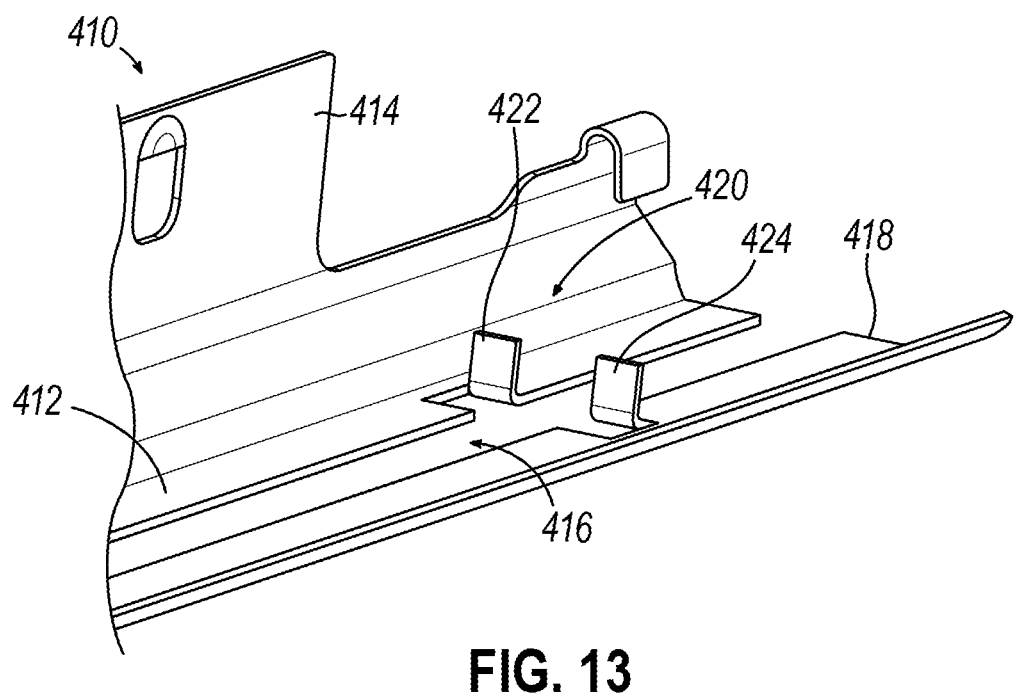
FIG. 13 depicts a partial perspective view of a cartridge tray of the staple cartridge of FIG. 12.

As best seen in FIGS. 12 and 13, staple cartridge (454) of the present example includes a cartridge tray (410) (also referred to as a pan). Although not described above, it should be understood that staple cartridge (154) may also include structures similar to cartridge tray (410) in some examples. Cartridge tray (410) of the present example is configured to snap-fit, clip, or otherwise couple to a lower portion of cartridge body (456). In some examples, cartridge tray (410) comprises a metallic material to provide added structural rigidity to staple cartridge (454).

Cartridge tray (410) of the present example includes a floor (412) and a pair of sidewalls (414) extending from a proximal end (418) of cartridge tray (410). A longitudinal slot (416) is defined by floor (412) extending from proximal end (418) of cartridge tray (410). Longitudinal slot (416) is generally configured to permit a portion of actuation assembly (164) to pass through cartridge tray (410) for engagement of second flange (185) with longitudinal slot (187) of lower jaw (152).

Cartridge tray (410) further includes a restriction feature (420). As will be described in greater detail below, restriction feature (420) is generally configured to manipulate wedge sled (470) to avoid premature and/or unintended actuation of wedge sled (470). In other words, restriction feature (420) is generally configured to prevent unintended movement of wedge sled (470), yet permit intended movement of wedge sled (470).

Restriction feature (420) of the present example includes a pair of retainers (422, 424) extending upwardly from floor (412). The particular extension of each retainer (422, 424) in the present example is generally about perpendicular to a longitudinal axis defined by floor (412), although other angles of extension relative to floor may be used in other examples. Each retainer (422, 424) is positioned proximate proximal end (418) of cartridge tray (410). As will be described in greater detail below, this positioning is generally configured to correspond to an initial positioning of wedge sled (470).

The construction of each retainer (422, 424) of the present example is integral with floor (412) and positioned on opposite sides of longitudinal slot (416). Specifically, each retainer (422, 424) is defined by a cutout portion of floor (412) that is bent upwardly or perpendicularly relative to the extension of floor (412). Thus, each retainer (422, 424) in the present example is generally of the same material of floor (412). As described above, the particular material used may be metal or other similarly rigid materials. Although an integral construction is used in the present example for each retainer (422, 424), it should be understood that in other examples each retainer (422, 424) may be an independent component from floor (412) and coupled thereto.

Each retainer (422, 424) in the present example is configured to have at least some rigidity. As will be described in greater detail below, such rigidity may permit each retainer (422, 424) to hold wedge sled (470) in a predetermined position. Additionally, such rigidity may also be configured in some examples to provide additional structural rigidity to cartridge tray (410), particularly at the interface between floor (412) and each retainer (422, 424).

Each retainer (422, 424) in the present example is also configured to have at least some flexibility. As will also be described in greater detail below, such flexibility may permit each retainer (422, 424) to move in response to movement of wedge sled (470) driven by pusher member (166). In other words, each retainer (422, 424) may be configured to permit intentional movement of wedge sled (470) via flexibility of each retainer (422, 424), yet prevent incidental movement of wedge sled (470) via rigidity of each retainer (422, 424).

Figure 14A:
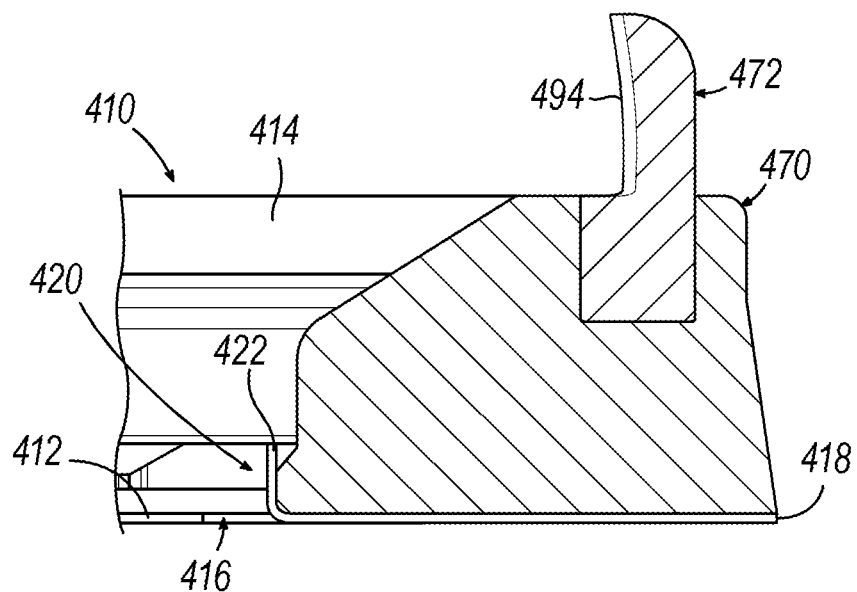
FIG. 14A depicts a side cross-sectional view of the staple cartridge of FIG. 12, with a restriction feature blocking distal movement of a wedge sled of the staple cartridge.
Figure 14B:
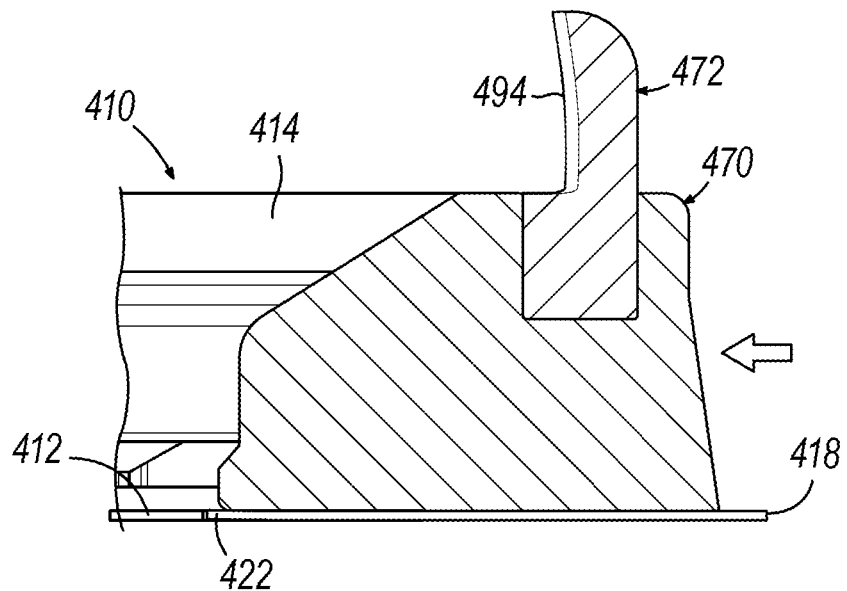
FIG. 14B depicts another side cross-sectional view of the staple cartridge of FIG. 12, with a portion of the restriction feature deformed to permit distal movement of the wedge sled of FIG. 14A.

FIGS. 14A and 14B show an exemplary use of restriction feature (420) in connection with wedge sled (470). As can be seen, wedge sled (470) begins proximate proximal end (418) of cartridge tray (410) with knife member (472) disposed within blade guard (455). This position of wedge sled (470) may also correspond to wedge sled (470) being proximate proximal end (476) of staple cartridge (454). In this position, restriction feature (420) is configured to prevent incidental movement of wedge sled (470) and thereby hold knife member (472) within blade guard (455). Specifically, each retainer (422, 424) is oriented approximately perpendicularly relative to floor (412). As can be seen in FIG. 14A, this orientation blocks distal movement of wedge sled (470), thereby holding wedge sled (470) proximate proximal end (418) and within blade guard (455).

As described above, wedge sled (470) may be driven distally within cartridge body (456) to drive staples using wedge sled (470) and server tissue using cutting edge (494) of knife member (472). As similarly described above with respect to wedge sled (170), wedge sled (470) of the present example may be similarly driven by pusher member (166). As seen in FIG. 14B, once wedge sled (470) is driven by pusher member (166), the force supplied by pusher member (166) may be sufficient to overcome the rigidity of each retainer (422, 424). This causes each retainer (422, 424) to move and/or pivot away from wedge sled (470) from the upward orientation described above to a horizontal position about parallel to the extension of floor (412).

Once each retainer (422, 424) is pushed to the horizontal position, wedge sled (470) may be driven distally by pusher member (166) to drive staples and sever tissue. In the present example, each retainer (422, 424) is generally configured to bend in response to wedge sled (470) being driven by pusher member (166). In other words, each retainer (422, 424) is deformed by wedge sled (470) such that each retainer (422, 424) may remain in the horizontal position after wedge sled (470) has been driven distally past each retainer (422, 424). This configuration may be desirable in some examples to, for example, prevent reuse of staple cartridge (454).

In other examples, each retainer (422, 424) may alternatively have a resilient characteristic such that each retainer (422, 424) may return to the upwardly extended position after wedge sled (470) has been driven distally past each retainer (422, 424). In other words, each retainer (422, 424) may be resiliently biased toward the upwardly extended position described above. In such examples, this resilient characteristic may be desirable to promote structural stability of cartridge tray (410) during actuation of wedge sled (470) distally. Examples of suitable cartridge trays (410) having resilient characteristics are described in U.S. patent application Ser. No. 17/402,695, entitled "Firing System Features for Surgical Stapler," filed on Aug. 16, 2021, published as U.S. Pub. No. 2023/0050707 on Feb. 16, 2023, the disclosure of which is hereby incorporated by reference herein in its entirety.

B. Exemplary Alternative Staple Cartridge with Movable Restriction Feature

Figure 15:
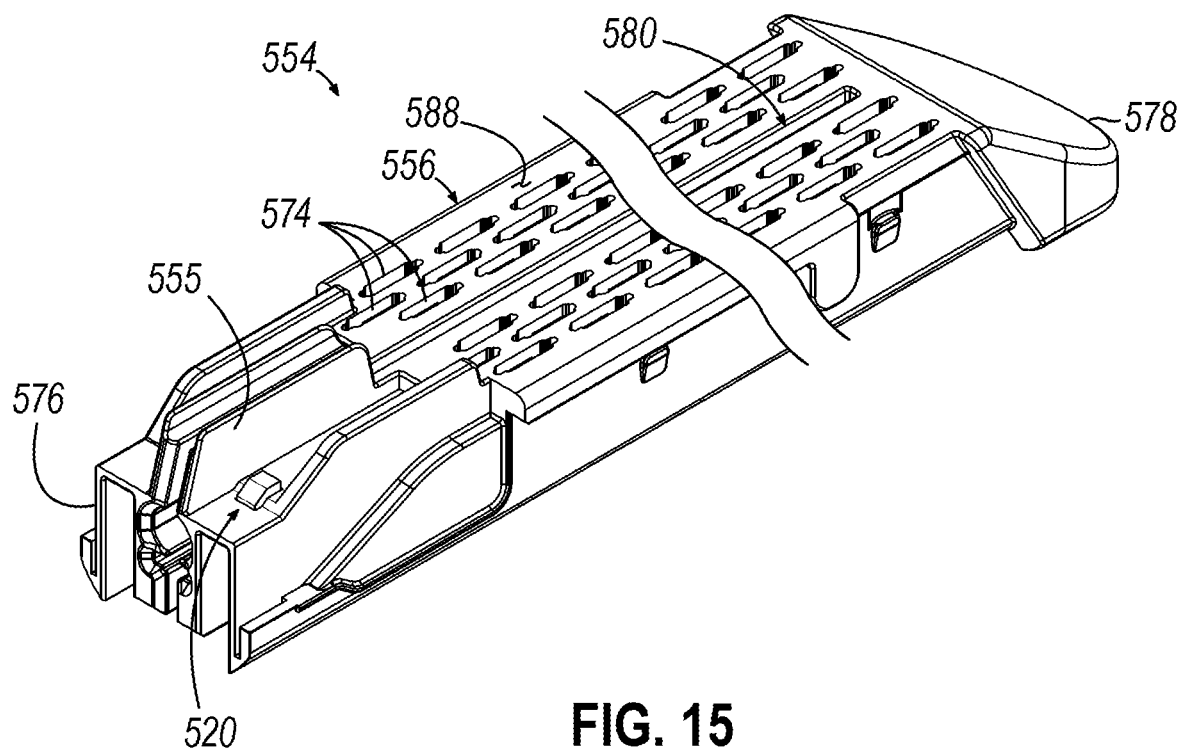
FIG. 15 depicts a perspective view of another exemplary alternative staple cartridge for use with the surgical instrument of FIG. 4.

FIG. 15 shows an exemplary alternative staple cartridge (554) that may be readily used with end effector (116, 210) described above in lieu of staple cartridges (154, 254). Staple cartridge (554) is substantially similar to staple cartridge (154) described above, unless where otherwise noted herein. For instance, like with staple cartridge (154), staple cartridge (554) of the present example includes a staple cartridge body (556) that is configured to house a firing assembly (558), a plurality of staple drivers (not shown), and a plurality of staples (not shown). As with firing assembly (158) described above, firing assembly (558) of the present example includes a wedge sled (570) and a knife member (572) (see FIG. 19A).

Staple cartridge body (556) of the present example is similar to staple cartridge body (156) in that staple cartridge body (556) includes an array of staple accommodating apertures (574) extending through an upper deck (588) of staple cartridge body (556). Staple cartridge (554) includes proximal and distal ends (576, 578). In operation, staples (not shown) are sequentially deployed starting at proximal end (576) by advancing wedge sled (570) toward distal end (578) from proximal end (576). A vertical slot (580) configured to accommodate knife member (572) through part of staple cartridge (554) to permit a cutting edge (594) to cut tissue as the staples are driven via wedge sled (570).

Staple cartridge (554) further includes a blade guard (555) (also referred to as a cover, sheath, and/or compartment). Blade guard (555) extends upwardly from upper deck (588) and is disposed at a proximal end of cartridge body (556). In the present example, blade guard (555) is defined by two upwardly extending slats disposed on each side of vertical slot (580). As will be understood, blade guard (555) is configured to contain knife member (572) to avoid inadvertent contact with cutting edge (594) when staple cartridge (554) is not in use. As such, the particular position of blade guard (555) relative to cartridge body (556) corresponds to a proximal or home position of wedge sled (570).

Unlike staple cartridge (154) described above, staple cartridge (554) of the present example includes a restriction feature (520). Restriction feature (520) is generally configured to move within cartridge body (556) to selectively lock and unlock movement of wedge sled (570). As will be described in greater detail below, a portion of restriction feature (520) is generally configured to protrude from a portion of cartridge body (556) proximate blade guard (555). This portion of restriction feature (520) is generally configured to engage a portion of end effector (116, 210) to move at least a portion of restriction feature (520) and thereby unlock movement of wedge sled (570).

Figure 16:
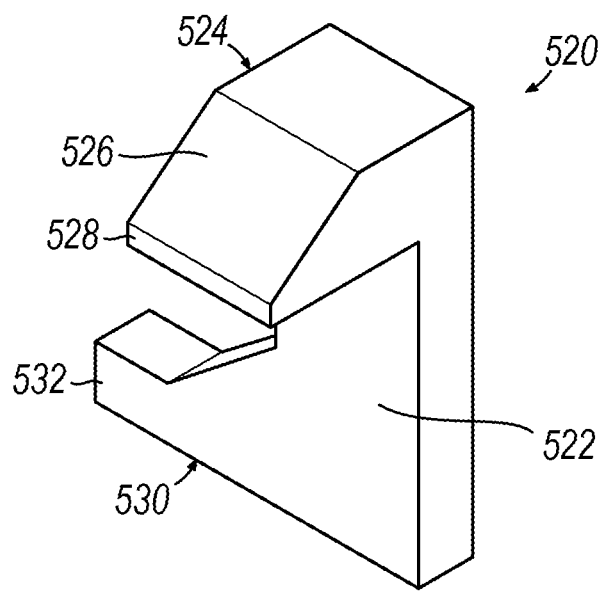
FIG. 16 depicts a perspective view of a restriction feature of the staple cartridge of FIG. 15.

As best seen in FIG. 16, restriction feature (520) includes a body having an actuation portion (524) and a lock portion (530). Actuation portion (524) includes a proximal ramp (526) and a catch (528). Proximal ramp (526) is generally configured to engage a portion of end effector (116, 210) to drive movement of restriction feature (520). The orientation of proximal ramp (526) is such that a face is positioned toward proximal end (576) of staple cartridge (554). As will be understood, this orientation is generally configured to promote engagement between proximal ramp (526) and a portion of end effector (116, 210). Proximal ramp (526) is also oriented at an angle relative to the longitudinal extension of upper deck (588). Proximal ramp (526) may be oriented at a variety of suitable angles. For instance, in some examples, proximal ramp (526) may be oriented at 35°, 45°, 65° or other suitable angles relative to the longitudinal extension of upper deck (588).

Catch (528) extends downwardly from proximal ramp (526). In the present example, catch (528) is configured to engage at least a portion of upper deck (588) to provide at least some resistance to movement of restriction feature (520). In some circumstances, this feature may be desirable to avoid inadvertent movement of restriction feature (520). Catch (528) of the present example is configured as a L-shaped ledge, shelf, or protrusion extending from proximal ramp (526). In other examples, catch (528) may take on a variety of forms such as one or more rounded or square-shaped detent, one or more ribs, and/or etc. In other examples, catch (528) may be more or less prominent than the version shown. For instance, in some examples catch (528) may protrude minimally or not at all from proximal ramp (526). Instead, catch (528) may simply be a roughened or knurled surface configured to engage upper deck (588). In still other examples, catch (528) may be omitted entirely.

As described above, lock portion (530) includes a lock member (532). As will be described in greater detail below, lock member (532) is generally configured to selectively engage a portion of wedge sled (570) to restrict movement of wedge sled (570) within cartridge body (556). Lock member (532) is disposed on an opposite end of body (522) relative to actuation portion (524), proximal ramp (526), and/or catch (528). Specifically, body (522) extends downward or laterally away from upper deck (588) from actuation portion (524) towards lock portion (530). Additionally, lock member (532) extends outwardly or perpendicularly relative to an extension axis of body (522). In the present example, lock member (532) defines a generally rectangular shape, although it should be understood various alternative shapes may be used in other examples.

Referring to FIG. 15, restriction feature (520) extends through a portion of upper deck (588) for actuation of restriction feature (520) from an exterior of cartridge body (556) and for engagement between restriction feature (520) and wedge sled (570) within cartridge body (556). In particular, at least a portion of actuation portion (524) rests on an upper surface of upper deck (588) exposing proximal ramp (526) to the exterior of cartridge body (556). Body (522) of restriction feature (520) then extends downwardly though upper deck (588) into the interior of cartridge body (556). As will be described in greater detail below, inside cartridge body (556), lock portion (530) or restriction feature (520) may selectively engage wedge sled (570) to selectively prevent movement of wedge sled (570). To facilitate such an extension through upper deck (588), in some examples upper deck (588) may include an opening, channel, bore, void, chamber, or other spaces configured to receive one or more portions of restriction feature (520).

The particular orientation of restriction feature (520) relative to upper deck (588) generally corresponds to the position of wedge sled (570) prior to actuation. In other words, restriction feature (520) is positioned to engage wedge sled (570) when wedge sled (570) is proximate proximal end (576) of staple cartridge (554). Additionally, restriction feature (520) is generally positioned off-center and/or laterally offset relative to a central longitudinal axis extending through staple cartridge (554). In other words, restriction feature (520) is offset towards a particular side of staple cartridge (554). The particular position of restriction feature (520) in the present example is generally configured to promote selective engagement between restriction feature (520) and wedge sled (570). Thus, it should be understood that in other examples, a variety of alternative orientations may be used for restriction feature (520) sufficient to promote selective engagement between restriction feature (520) and wedge sled (570).

Figure 17:
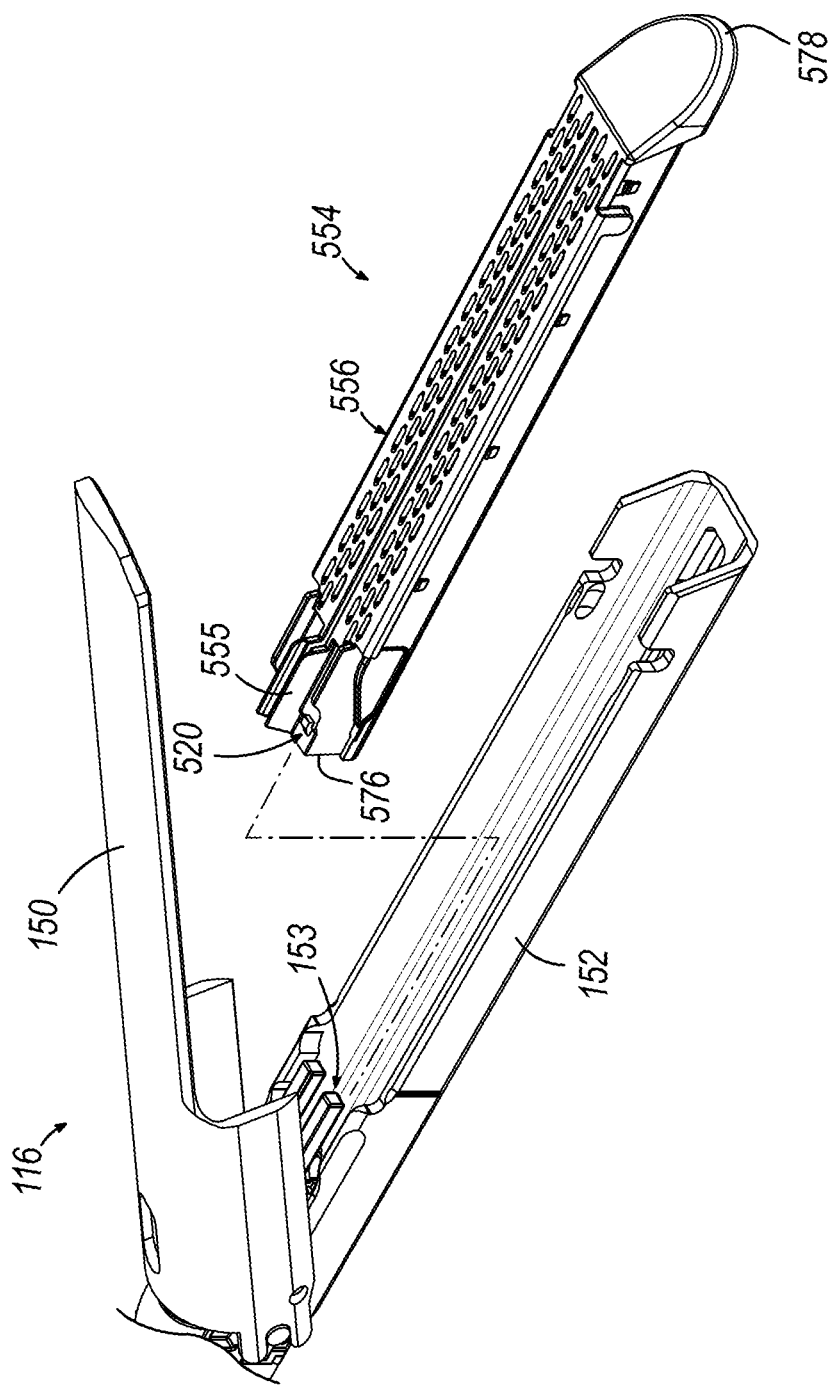
FIG. 17 depicts a perspective view of the end effector of FIG. 4, the end effector in an open configuration.

FIG. 17 shows an alternative view of end effector (116) described above. As can be seen, end effector (116) includes an inner support member (153) (also referred to as a strut, frame member, or protrusion). Inner support member (153) is associated with lower jaw (152) and/or upper jaw (150) and extends along an inner surface of lower jaw (152) between and lower jaw (152) and upper jaw (150). Inner support member (153) may be used for a variety of purposes. For instance, in some examples, inner support member (153) may be configured to promote movement of lower jaw (152) relative to upper jaw (150). In addition, or in the alternative, support member (153) may be configured to provide support to staple cartridge (554) during closure of end effector (116). Still other purposes for inner support member (153) will be apparent to those of ordinary skill in the art in view of the teachings herein.

Regardless of the particular purpose of inner support member (153) in the context of end effector (116), inner support member (153) in the present example may be configured to engage a portion of restriction feature (520). As will be described in greater detail below, restriction feature (520) is generally movable laterally into cartridge body (556) and away from lower jaw (152). As such, in some examples, inner support member (153) may be configured to manipulate restriction feature (520).

FIGS. 18A through 19B show an exemplary use of staple cartridge (554) of the present example in connection with end effector (116) described above. Although the use shown and described herein is in connection with end effector (116), it should be understood that in other uses the same steps and/or principles described herein may be readily applied to use with end effector (210) described above.

Figure 18A:
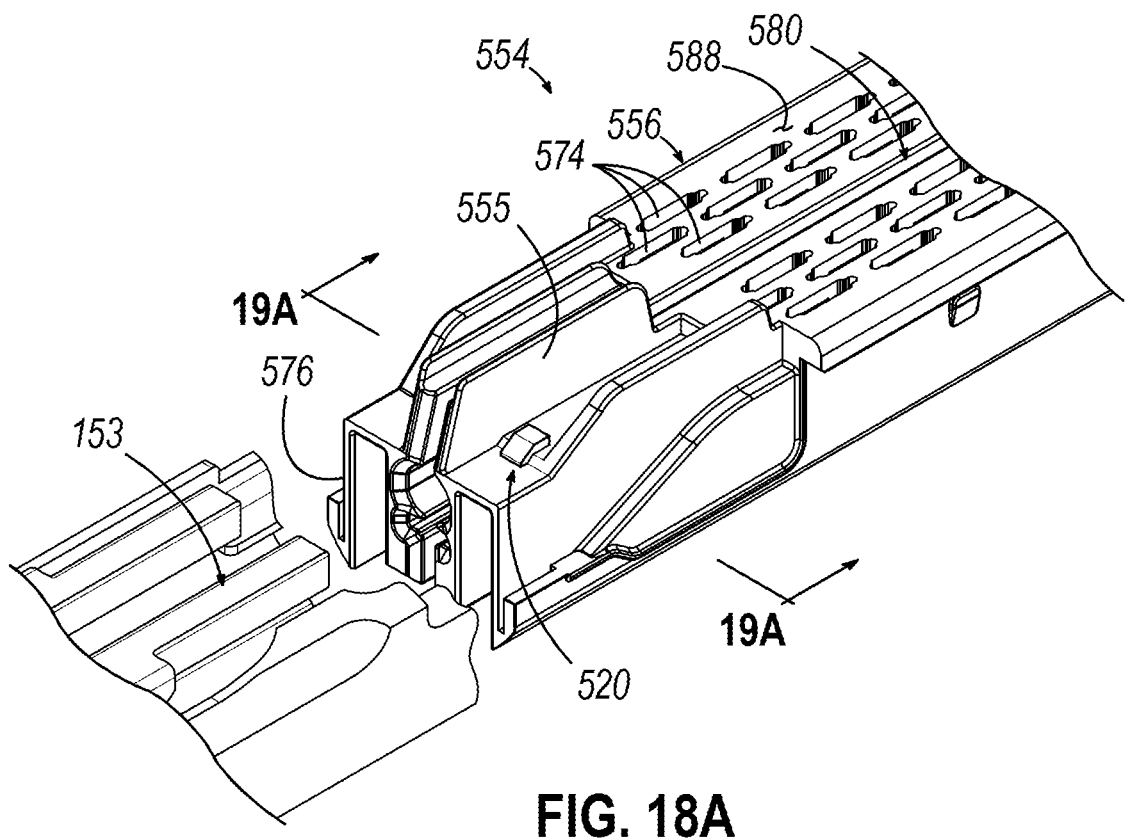
FIG. 18A depicts a partial perspective view of the staple cartridge of FIG. 15 being inserted within the end effector of FIG. 4.
Figure 19A:
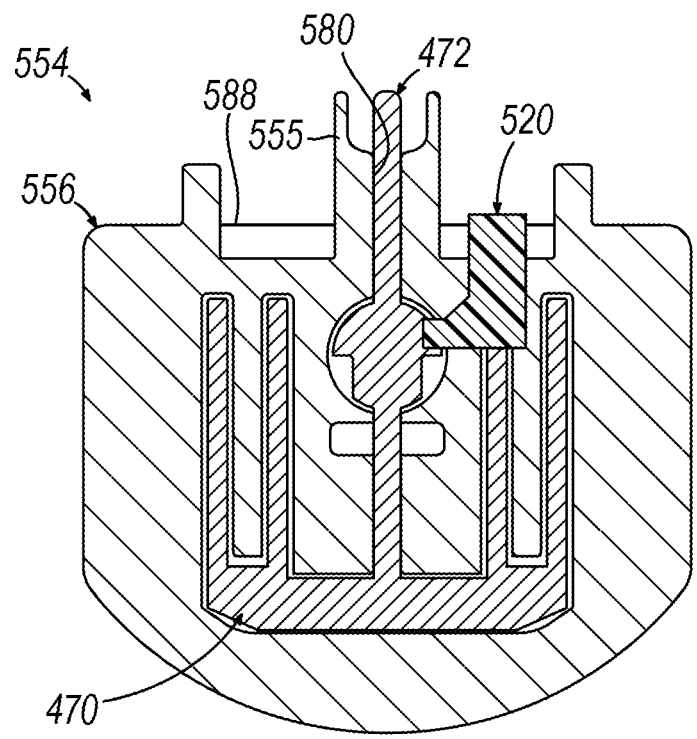
FIG. 19A depicts a front cross-sectional view of the staple cartridge of FIG. 15 inserted within the end effector of FIG. 4, the restriction feature of FIG. 16 being in a locked position.

As best seen in FIG. 18A, staple cartridge (554) is initially inserted into lower jaw (152). At this stage, restriction feature (520) is positioned in an initially locked position. In this position, restriction feature (520) is positioned such that lock member (532) is disposed in engagement with wedge sled (570) to prevent distal movement of wedge sled (570) from proximal end (576) to distal end (578) of staple cartridge (554). This position of restriction feature (520) is generally desirable to hold knife member (572) within blade guard (555). Specifically, as best seen in FIG. 19A, lock member (532) is positioned to engage a portion of knife member (572) to prevent distal movement of wedge sled (570) and hold knife member (572) within blade guard (555). This locked position may be desirable to prevent inadvertent contact with cutting edge (594) due to unexpected movement of wedge sled (570) during installation of staple cartridge (554) or other preliminary procedures.

Figure 18B:
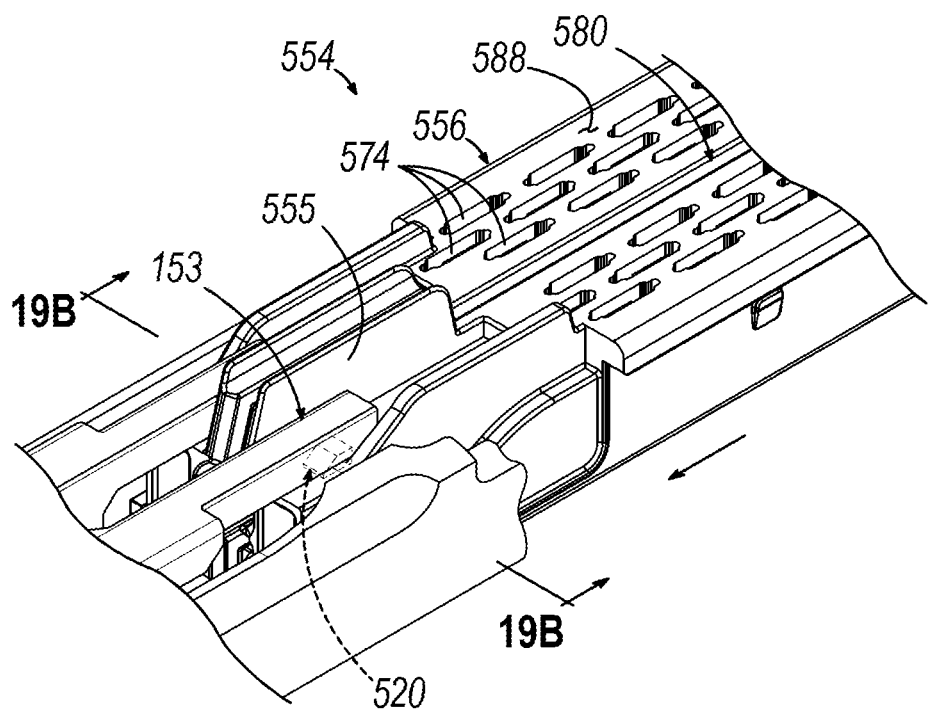
FIG. 18B depicts a partial perspective view of the staple cartridge of FIG. 15 disposed within the end effector of FIG. 4 and a portion of the end effector being used to actuate the restriction feature of FIG. 16.

While restriction feature (520) is positioned in the locked position, staple cartridge (554) can be installed within lower jaw (152) as shown in FIG. 18B. Once staple cartridge (554) is installed within lower jaw (152), restriction feature (520) may transition from the locked position to the unlocked position. As best seen in FIG. 18B, during insertion of staple cartridge (554), inner support member (153) engages proximal ramp (526) of restriction feature (520). Engagement between inner support member (153) and proximal ramp (526) causes movement of restriction feature (520) downwardly and/or away from lower jaw (152) and into cartridge body (556) into the position shown in FIG. 19B. Although inner support member (153) is described herein as being used to engage proximal ramp (526), it should be understood that in other examples, other portions of end effector (116) may be used to engage proximal ramp (526). For instance, in some examples, lower jaw (152) may include one or more features extending therefrom specifically configured to engage proximal ramp (526). In still other examples, various other components of end effector (116) may be used to engage proximal ramp (526) including, for example, dedicated components or assemblies configured to actuate restriction feature (520).

Although transition of restriction feature (520) from the locked position to the unlocked position is shown in the present example as corresponding to insertion of staple cartridge (554) into lower jaw (152), in some uses this transition may occur at other stages of use. For instance, in some examples, restriction feature (520) may remain in the locked position after insertion of staple cartridge (554). This may be desirable in the present use to prevent unintentional contact with cutting edge (594) prior to cutting and stapling of tissue. In such a use, restriction feature (520) may be moved to the unlocked position using closure of end effector (116). For instance, as end effector (116) closes, upper jaw (150) moves in closer proximity to lower jaw (152). This movement may be used to actuate restriction feature (520) using a feature similar to inner support member (153), but associated with upper jaw (150) instead of lower jaw (152).

Figure 19B:
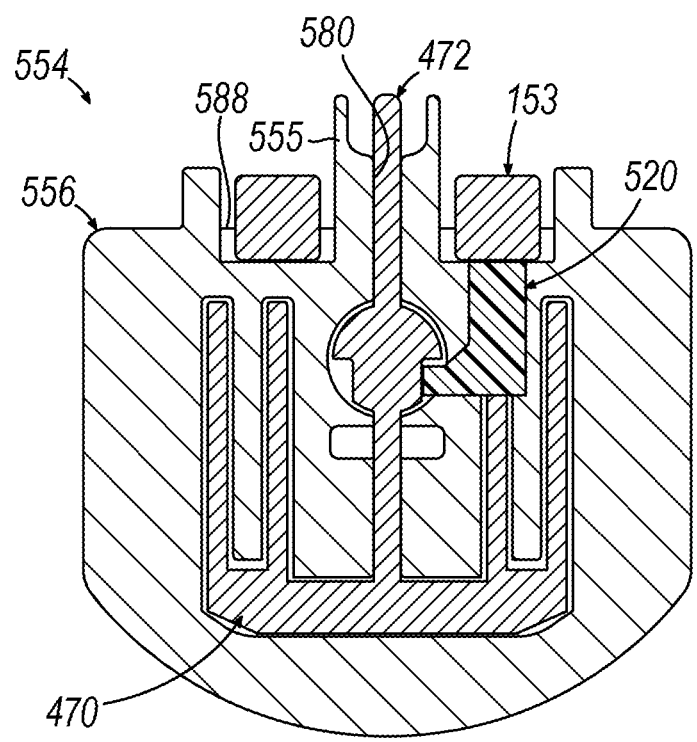
FIG. 19B depicts another front cross-sectional view of the staple cartridge of FIG. 15 inserted within the end effector of FIG. 4, the restriction feature of FIG. 16 being in an unlocked position.

Regardless of how proximal ramp (526) is engaged, such engagement may cause restriction feature (520) to transition from the locked position to the unlocked position. As can be seen in FIG. 19B, once restriction feature (520) is transitioned to the unlocked position, lock member (532) is moved out of engagement with wedge sled (570). This movement permits distal movement of wedge sled (570) within cartridge body (556). Thus, once restriction feature (520) is moved to the unlocked position, wedge sled (570) may be freely actuated by pusher member (166) to drive one or more staples and/or sever tissue.

Although not shown, it should be understood that in some examples, restriction feature (520) may include a resilient feature such as a spring to bias restriction feature (520) towards the locked position. In such examples, movement of wedge sled (570) may thus be unlocked upon closure of end effector (116). Upon reopening of end effector (116), movement of wedge sled (570) may then be locked due to the spring bias of restriction feature (520). Such a spring bias may be desirable to promote reuse of staple cartridge (554) either in a single procedure or in one or more follow-up procedures. Of course, in circumstances where prevention of reuse of staple cartridge (554) is desired, such a spring bias may be omitted entirely.

C. Exemplary Alternative Staple Cartridge with Slidable Restriction Feature

Figure 20:
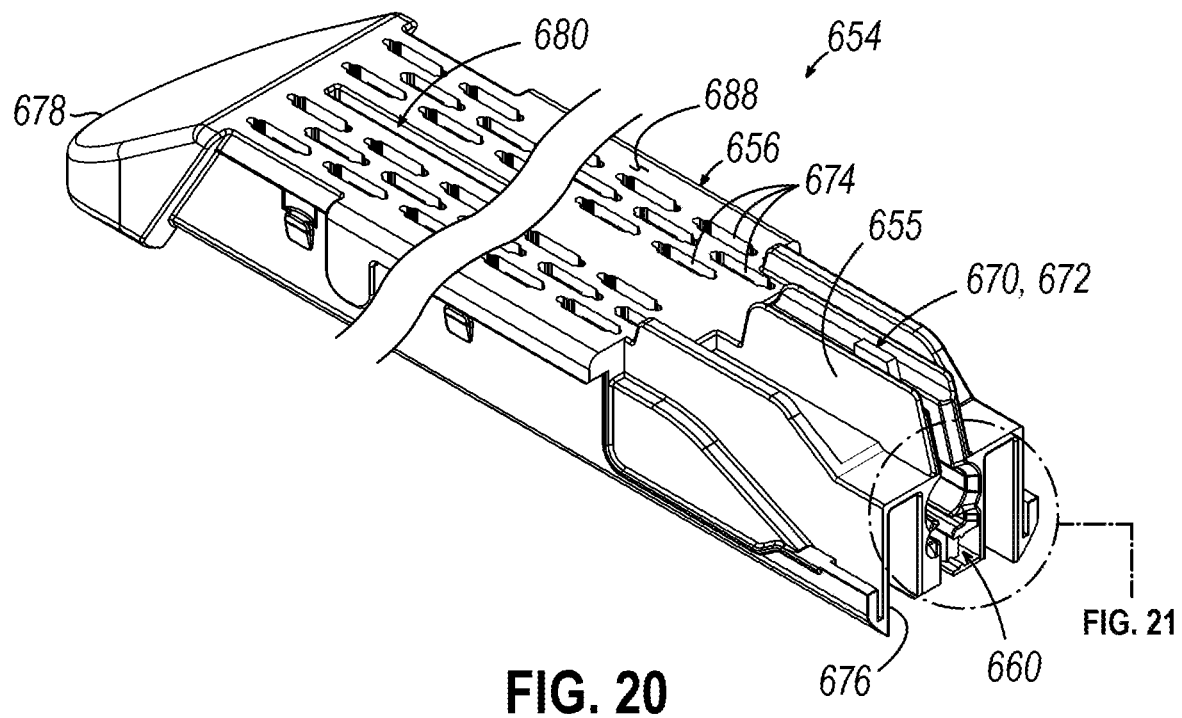
FIG. 20 depicts a partial perspective view of another exemplary alternative staple cartridge for use with the surgical instrument of FIG. 4.

FIG. 20 shows an exemplary alternative staple cartridge (654) that may be readily used with end effector (116, 210) described above in lieu of staple cartridges (154, 254). Staple cartridge (654) is substantially similar to staple cartridge (154) described above, unless where otherwise noted herein. For instance, like with staple cartridge (154), staple cartridge (654) of the present example includes a staple cartridge body (656) that is configured to house a firing assembly (658), a plurality of staple drivers (not shown), and a plurality of staples (not shown). As with firing assembly (158) described above, firing assembly (658) of the present example includes a wedge sled (670) and a knife member (672) (see FIG. 24A).

Staple cartridge body (656) of the present example is similar to staple cartridge body (156) in that staple cartridge body (656) includes an array of staple accommodating apertures (674) extending through an upper deck (688) of staple cartridge body (656). Staple cartridge (654) includes proximal end (676) and a distal end (not shown). In operation, staples (not shown) are sequentially deployed starting at proximal end (676) by advancing wedge sled (670) toward the distal end from proximal end (676). A vertical slot (680) configured to accommodate knife member (672) through part of staple cartridge (654) to permit a cutting edge (694) to cut tissue as the staples are driven via wedge sled (670).

Staple cartridge (654) further includes a blade guard (655) (also referred to as a cover, sheath, and/or compartment). Blade guard (655) extends upwardly from upper deck (688) and is disposed at a proximal end of cartridge body (656). In the present example, blade guard (655) is defined by two upwardly extending slats disposed on each side of vertical slot (680). As will be understood, blade guard (655) is configured to contain knife member (672) to avoid inadvertent contact with cutting edge (694) when staple cartridge (654) is not in use. As such, the particular position of blade guard (655) relative to cartridge body (656) corresponds to a proximal or home position of wedge sled (670).

Figure 21:
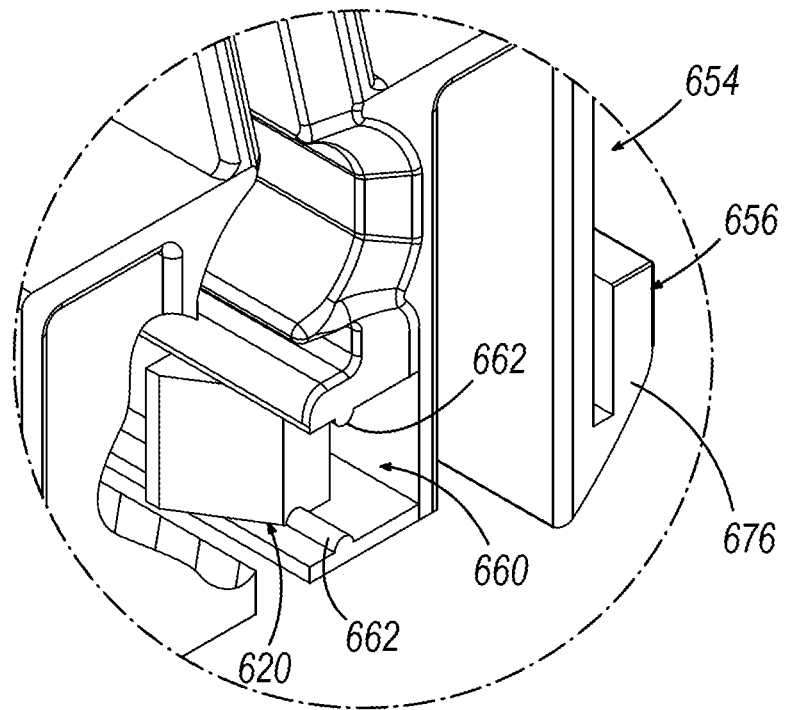
FIG. 21 depicts a detailed perspective view of a proximal end of the staple cartridge of FIG. 20.

Unlike staple cartridge (154) described above, staple cartridge (654) of the present example includes a restriction feature (620). Restriction feature (620) is generally configured to resist movement of wedge sled (670) to prevent inadvertent advancement of wedge sled (670). In the present example, restriction feature (620) is received within a proximal channel (660) defined by cartridge body (656). As best seen in FIG. 21, proximal channel (660) defines a U-shaped cross-section and extends distally though at least a portion of cartridge body (656). Although proximal channel (660) in the present example is defined by cartridge body (656), it should be understood that in other examples proximal channel (660) may be defined by other suitable components of staple cartridge (654).

Cartridge body (656) includes one or more detent features (662) extending into a portion of proximal channel (660). Detent features (662) are generally configured to releasably hold restriction feature (620) in a predetermined position. Specifically, the present example includes a detent feature (662) extending downwardly into a portion of proximal channel (660) and a detent feature (662) extending upwardly into a portion of proximal channel (660). In this configuration, detent features (662) engage a top and bottom portion of restriction feature (620) to releasably hold restriction feature (620) in a predetermined position.

Each detent feature (662) of the present example includes a protrusion defining a semi-circular cross-section. Each detent feature (662) also extends longitudinally along the axis of extension of proximal channel (660). In some examples, each detent feature (662) may extend along the entire length of proximal channel (660). In other examples, each detent feature (662) may extend along only a portion of proximal channel (660). In still other examples, each detent feature (662) may instead be configured as a plurality of individual bumps or hemispheres arranged in a line oriented parallel to the extension of proximal channel (660). Of course, other configurations of detent features (662) suitable to releasably hold restriction feature (620) in position will be apparent to those of ordinary skill in the art in view of the teachings herein.

Figure 22:
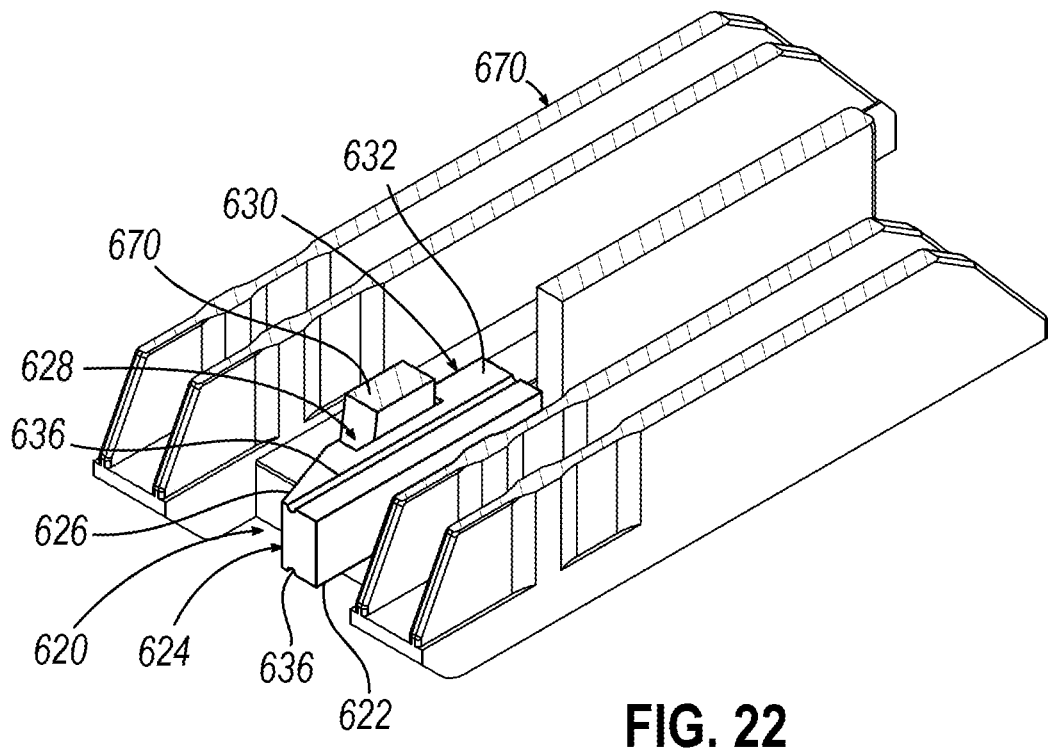
FIG. 22 depicts a partial perspective cross-sectional view of the staple cartridge of FIG. 20.
Figure 23:
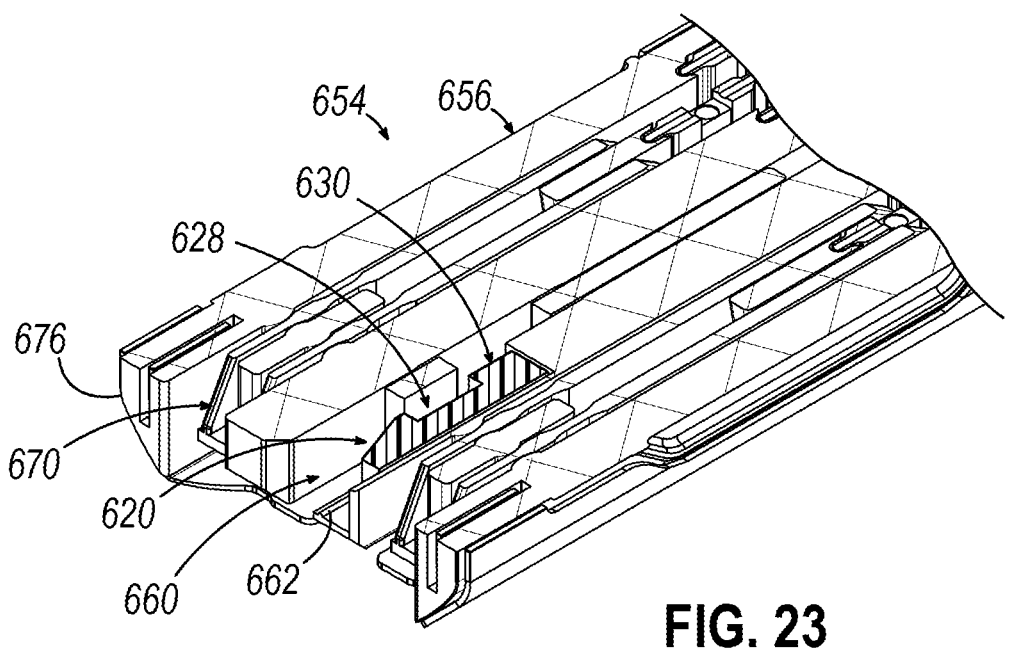
FIG. 23 depicts another partial perspective cross-sectional view of the staple cartridge of FIG. 20.

As best seen in FIG. 22, restriction feature (620) includes a body (622) having an actuation portion (624) and a lock portion (630) with a notch (628) disposed between actuation portion (624) and lock portion (630). Actuation portion (624) includes a proximal ramp (626) (also referred to as a cam surface) disposed on a proximal end of restriction feature (620). Proximal ramp (626) defines a ramped surface oriented proximally and at an angle such that proximal ramp (626) extends in cross-section from the proximal end of proximal ramp (626) to the distal end of proximal ramp (626). As will be described in greater detail below, proximal ramp (626) is generally configured to engage portions of actuation assembly (164), such as pusher member (166), to drive movement of restriction feature (620) away from wedge sled (670).

Lock portion (630) is disposed opposite of actuation portion (624) proximate a distal end of restriction feature (620). As will be described in greater detail below, lock portion (630) is generally configured to restrict movement of wedge sled (670). In the present example, lock portion (630) includes a lock member (632) generally configured to engage at least a portion of wedge sled (670) to restrict movement of wedge sled (670). The particular shape of lock member (632) of the present example is generally a square or rectangular shape, although other shapes suitable to restrict movement of wedge sled (670) may be used.

As described above, body (622) defines a notch (628) between actuation portion (624) and lock portion (630). Notch (628) is generally configured to receive at least a portion of wedge sled (670). The particular depth of notch (628) as defined by body (622) is configured to permit engagement between at least a portion of wedge sled (670) and lock member (632) when wedge sled (670) is disposed within notch (628). Although notch (628) is shown in the present example as having a U-shape or rectangular shape, it should be understood that in other examples various alternative shapes suitable to receive a portion of wedge sled (670) may be used.

Restriction feature (620) further includes a retaining feature (636) extending from the distal end of body (622) to the proximal end of body (622). Retaining feature (636) is generally complementary in shape to detent feature (662) described above. In other words, retaining feature (636) and detent feature (662) are configured to operate cooperatively to releasably hold restriction feature (620) in a predetermined position. Consequently, retaining feature (636) defines an indentation within body (622) of a shape corresponding to detent feature (662). As described above, detent feature (662) defines a semi-circular cross-section. Thus, retaining feature (636) of the present example likewise defines a simi-circular cross-section configured to receive detent feature (662). Of course, in other examples where the shape of detent feature (662) is varied, the shape of retaining feature (636) may likewise be varied.

Although FIG. 22 shows retaining feature (636) being disposed on one side of body (622), it should be understood that a similar retaining feature (636) may be disposed on an opposite side of body (622). Although the present example includes retaining feature (636) as an indentation and detent feature (662) as a protrusion, it should be understood that in other examples the configuration may be reversed with retaining feature (636) being a protrusion and detent feature (662) being an indentation. In other examples, retaining feature (636) and detent feature (662) may be omitted entirely and instead the same functionality may be achieved via an interference fit between restriction feature (620) and cartridge body (656).

Figure 24A:
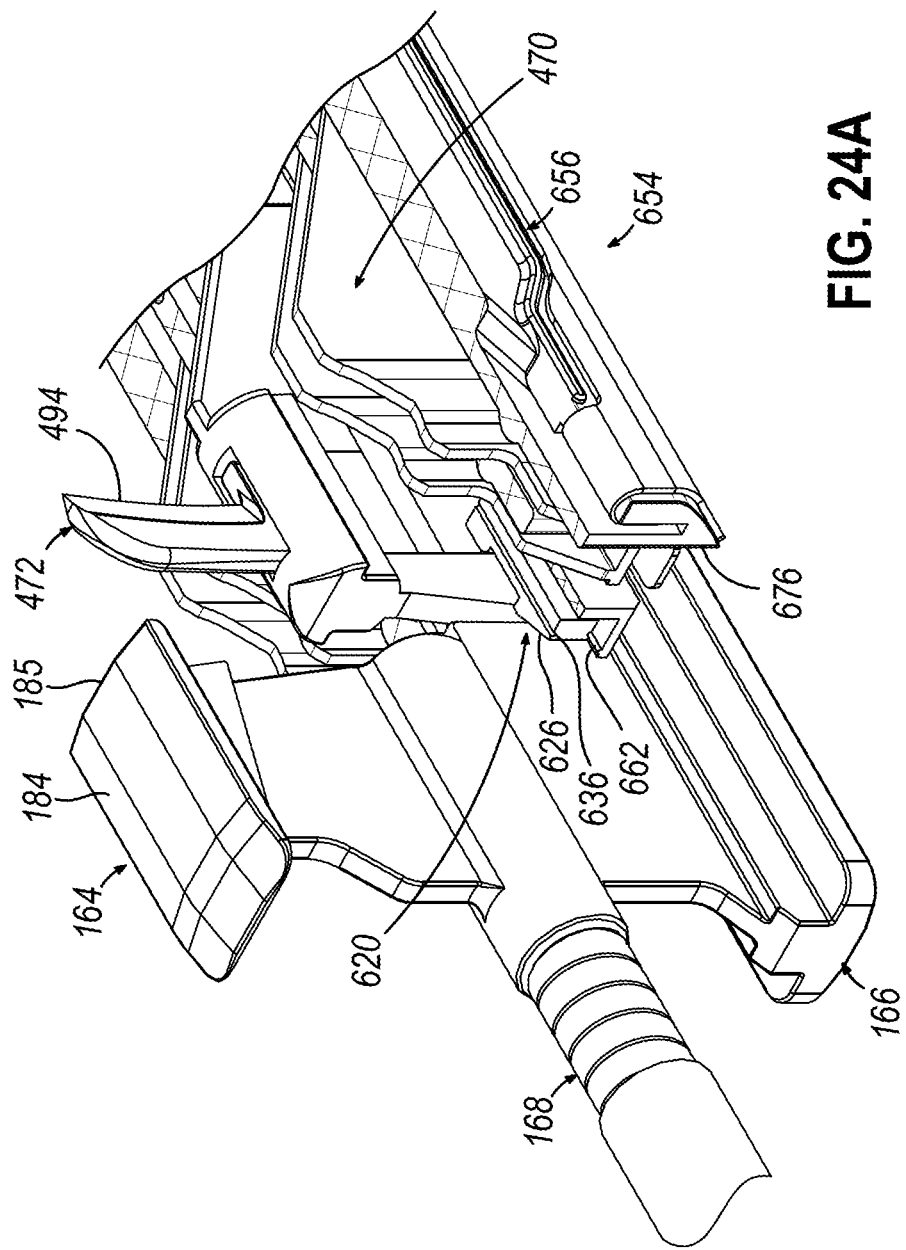
FIG. 24A depicts a partial perspective view of the staple cartridge of FIG. 20, with portions of the staple cartridge removed to show engagement between a restriction member of the staple cartridge and a pusher member of the end effector of FIG. 4, the restriction member in a locked position.
Figure 24B:
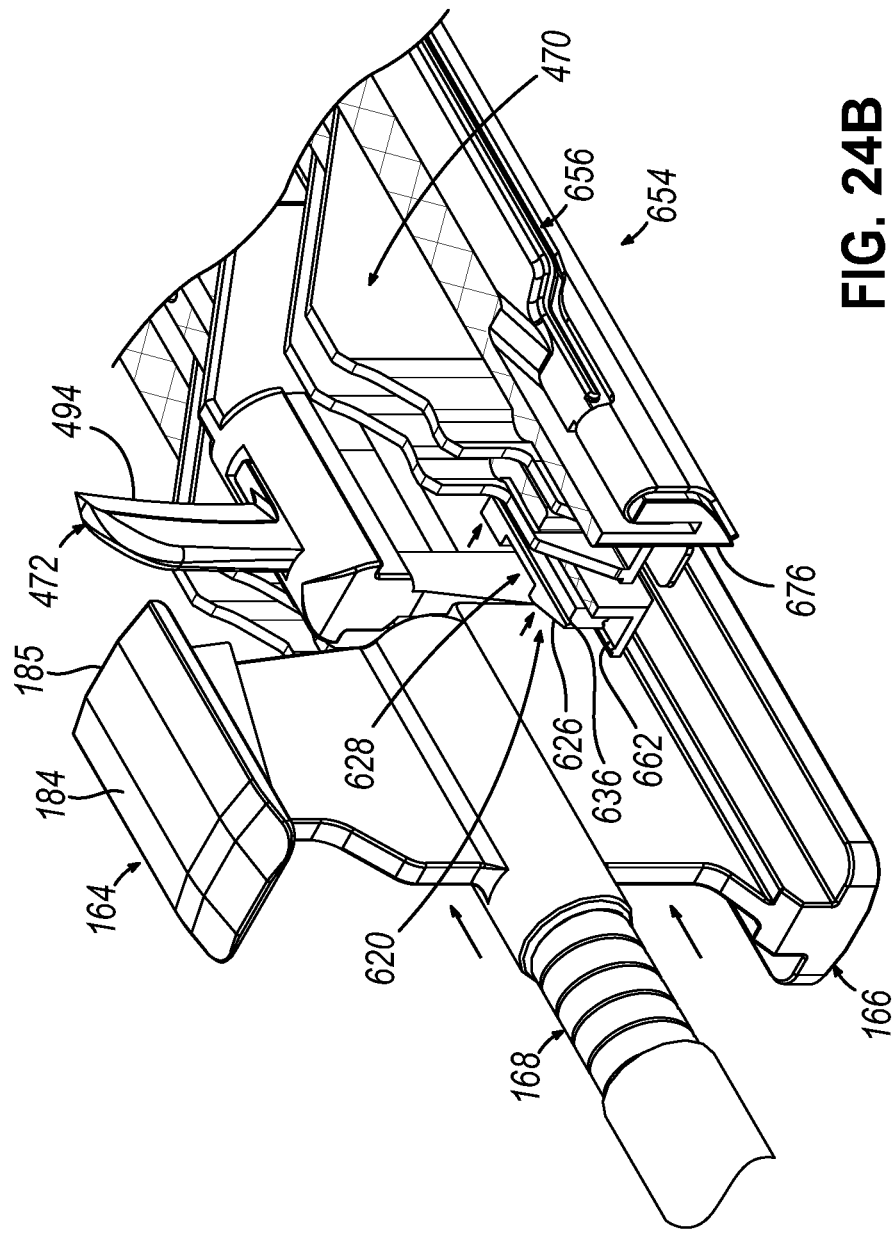
FIG. 24B depicts another partial perspective view of the staple cartridge of FIG. 20, with portions of the staple cartridge removed to show engagement between the restriction member of FIG. 24A and the pusher member of the end effector of FIG. 4, the restriction member in an unlocked position.

FIGS. 24A and 24B show an exemplary use of restriction feature (620). As can be seen, restriction feature (620) may begin in an initially locked position as shown in FIG. 24A. In this position, at least a portion of wedge sled (670) is received within notch (628) of restriction feature (620). With at least a portion of wedge sled (670) received within notch (628), movement of wedge sled (670) distally relative to cartridge body (656) is generally prevented via engagement between lock member (632) and wedge sled (670). This prevention of movement of wedge sled (670) holds knife member (672) of wedge sled (670) within blade guard (655) to prevent inadvertent contact with cutting edge (694). Additionally, restriction feature (620) is held in the locked position via engagement between retaining feature (636) and detent feature (662).

Restriction feature (620) may be shifted from the locked position to an unlocked position upon firing of wedge sled (670) via actuation assembly (164). Specifically, as best seen in FIG. 24B, pusher member (166) of actuation assembly (164) may be moved distally to move wedge sled (670) distally. Distal movement of actuation assembly (164) may result in engagement between pusher member (166) and restriction feature (620). Specifically, a portion of pusher member (166) may contact proximal ramp (626) of restriction feature (620), thereby overcoming engagement between retaining feature (636) and detent feature (662) and pushing restriction feature (620) laterally away from both pusher member (166) and wedge sled (670).

Once restriction feature (620) is pushed laterally as shown in FIG. 24B, wedge sled (670) may no longer be disposed within notch (628). With wedge sled (670) no longer disposed within notch (628), wedge sled (670) may be disengaged from lock member (623). Once lock member (623) is disengaged from wedge sled (670), restriction feature (620) is in the unlocked position and wedge sled (670) may move distally relative to cartridge body (656) without restriction via restriction feature (620).

In the present example, restriction feature (620) may remain in the unlocked position after being transitioned from the locked position. This configuration may be desirable for single use applications where staple cartridge (654) is configured to be used only once and then replaced with another staple cartridge (654). However, it other examples, staple cartridge (654) may be configured for multi-use applications. In such applications, restriction feature (620) may be associated with a spring or other resilient member to bias restriction feature (620) toward the locked position. In such examples, the resilient feature may return restriction feature (620) to the locked position after pusher member (166) has passed restriction feature (620). Of course, in such examples restriction feature (620) may include other features such as distal ramps, cam surfaces, or the like to facilitate relocking upon retraction of wedge sled (670) and/or pusher member.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: a body; a shaft assembly extending distally from the body; an end effector disposed on a distal end of the shaft assembly, wherein the end effector includes a first jaw and a second jaw; a stapling assembly supported by one of the first jaw or the second jaw of the end effector, wherein the stapling assembly includes a wedge sled, wherein the wedge sled is configured to move relative to the one of the first jaw or the second jaw to drive movement of one or more staples; and a restriction feature, wherein the restriction feature is configured to releasably hold the wedge sled in a predetermined position within the stapling assembly while the stapling assembly is in a pre-fired configuration, wherein at least a portion of the restriction feature is configured to respond to movement of the wedge sled to release the restriction feature from the wedge sled.

Example 2

The surgical instrument of Example 1, wherein the stapling assembly comprises a staple cartridge configured to be received by the one of the first jaw or the second jaw, wherein the staple cartridge includes a cartridge body and a pan coupled to a portion of the cartridge body, wherein the pan includes one or more retainers defining the restriction feature.

Example 3

The surgical instrument of Example 2, wherein the pan includes a pan body extending along a first axis parallel to a longitudinal axis defined by the cartridge body, wherein the one or more retainers extend along a second axis oriented at an angle relative to the first axis.

Example 4

The surgical instrument of Examples 2 or 3, wherein the one or more retainers are configured to bend relative to a portion of the pan.

Example 5

The surgical instrument of any one or more of Examples 2 through 4, wherein the one or more retainers are integral with at least a portion of the pan.

Example 6

The surgical instrument of Example 1, wherein the restriction feature is configured to move relative to the cartridge body to selectively engage and disengage the wedge sled.

Example 7

The surgical instrument of Examples 1 or 6, wherein the restriction feature includes an actuation portion and a lock portion opposite the actuation portion, wherein the lock portion is configured to engage the wedge sled.

Example 8

The surgical instrument of Example 7, wherein the actuation portion includes a ramp, wherein the ramp is configured to engage at least a portion of the first jaw or the second jaw to drive movement of the lock portion relative to the wedge sled.

Example 9

The surgical instrument of Examples 7 or 8, wherein a portion of the stapling assembly defines an upper deck, wherein the actuation portion of the restriction feature protrudes from a portion of the upper deck.

Example 10

The surgical instrument of any one or more of Examples 7 through 9, wherein the actuation portion is configured to respond to movement of the first jaw relative to the second jaw to drive movement of the lock portion relative to the wedge sled.

Example 11

The surgical instrument of any one or more of Examples 7 through 10, wherein the stapling assembly includes a staple cartridge, wherein the staple cartridge is configured to be received in the first jaw, wherein the second jaw includes a support member, wherein movement of the first jaw relative to the second jaw is configured to actuate the actuation portion of the restriction feature via the support member while the staple cartridge is received within the first jaw.

Example 12

The surgical instrument of Example 7, wherein the restriction feature defines a notch disposed between the actuation portion and the lock portion, wherein the notch is configured to receive at least a portion of the wedge sled.

Example 13

The surgical instrument of Examples 6 or 7, wherein at least a portion of the stapling assembly defines a proximal channel, wherein the restriction feature is configured to be received within the proximal channel.

Example 14

The surgical instrument of Example 13, further comprising one or more detent features associated with the proximal channel or the restriction feature, wherein the detent features are configured to releasably hold the restriction feature in a predetermined position.

Example 15

The surgical instrument of Example 7, further comprising a pusher member in communication with a robotic arm, wherein the pusher member is configured to drive the wedge sled distally, wherein the pusher member is configured to engage the actuation portion of the restriction member to drive the restriction member laterally and thereby permit distal movement of the wedge sled.

Example 16

The surgical instrument of any one or more of Examples 1 through 14, wherein the body includes a coupler configured to communicate with a robotic arm.

Example 17

A surgical instrument, comprising: a body; a shaft assembly extending distally from the body; an end effector disposed on a distal end of the shaft assembly, wherein the end effector includes a first jaw and a second jaw; a stapling assembly associated with the first jaw or the second jaw of the end effector, wherein the stapling assembly includes a body defining a guard and a wedge sled, wherein the wedge sled is configured to move relative to the body from a pre-fired position to a fired position to drive movement of one or more staples; and a restriction feature configured to engage the wedge sled to releasably hold the wedge sled in a predetermined position proximate the blade while the stapling assembly is in the pre-fired position, wherein the restriction feature includes an actuation portion and a lock portion, wherein the actuation portion is configured to release the lock portion from a portion of the wedge sled.

Example 18

The surgical instrument of Example 17, wherein at least a portion of the actuation portion extends through an opening defined by the cartridge body, wherein the lock portion is disposed within an interior of the cartridge body.

Example 19

The surgical instrument of Examples 17 or 18, wherein the restriction feature is proximate the blade guard.

Example 19

The surgical instrument of Example 17, wherein the restriction feature is movable between a locked position and an unlocked position, wherein the restriction feature is biased towards the locked position.

Example 21

A method for use of a surgical instrument, the method comprising: inserting a staple cartridge into an end effector of the surgical instrument; restricting movement of a wedge sled associated with the staple cartridge during insertion of the staple cartridge into the end effector using a restriction feature to block movement of the wedge sled; and releasing movement of the wedge sled by moving at least a portion of the restriction feature relative to the wedge sled using movement of the wedge sled.

Example 22

The method of Example 21, wherein the step of releasing movement of the wedge sled includes applying a force to the wedge sled in a distal direction to deform at least a portion of the restriction feature.

Example 23

The method of Example 21, wherein the step of releasing movement of the wedge sled includes moving a portion of the end effector relative to the wedge sled to move the restriction feature relative to the wedge sled.

Example 24

The method of Example 21, wherein the step of releasing movement of the wedge sled includes moving a first jaw of the end effector relative to a second jaw of the end effector to move the restriction feature relative to the wedge sled using the first jaw or the second jaw.

Example 25

The method of Example 21, wherein the step of releasing movement of the wedge sled includes inserting the staple cartridge into the end effector to engage a portion of the end effector with a portion of the restriction feature to move the restriction feature relative to the wedge sled.

IV. Miscellaneous

Any one or more of the teachings, expressions, embodiments, examples, etc. described herein may be combined with any one or more of the teachings, expressions, embodiments, examples, etc. described in U.S. patent application Ser. No. 17/402,674, entitled "Methods of Operating a Robotic Surgical Stapler," filed on Aug. 16, 2021, published as U.S. Pub. No. 2023/0051361 on Feb. 16, 2023; U.S. patent application Ser. No. 17/402,675, entitled "Multi-Threshold Motor Control Algorithm for Powered Surgical Stapler," filed on Aug. 16, 2021, published as U.S. Pub. No. 2023/0051271 on Feb. 16, 2023; U.S. patent application Ser. No. 17/402,677, entitled "Variable Response Motor Control Algorithm for Powered Surgical Stapler," filed on Aug. 16, 2021, published as U.S. Pub. No. 2023/0048444 on Feb. 16, 2023; U.S. patent application Ser. No. 17/402,679, entitled "Powered Surgical Stapler Having Independently Operable Closure and Firing Systems," filed on Aug. 16, 2021, issued as U.S. Pat. No. 11,779,332 on Oct. 10, 2023; U.S. patent application Ser. No. 17/402,695, entitled "Firing System Features for Surgical Stapler," filed on Aug. 16, 2021, published as U.S. Pub. No. 2023/0050707 on Feb. 16, 2023; U.S. patent application Ser. No. 17/402,701, entitled "Multiple-Sensor Firing Lockout Mechanism for Powered Surgical Stapler," filed on Aug. 16, 2021, published as U.S. Pub. No. 2023/0050358 on Feb. 16, 2023; U.S. patent application Ser. No. 17/402,703, entitled "Proximally Located Firing Lockout Mechanism for Surgical Stapler," filed on Aug. 16, 2021, published as U.S. Pub. No. 2023/0051105 on Feb. 16, 2023; U.S. patent application Ser. No. 17/402,720, entitled "Cartridge-Based Firing Lockout Mechanism for Surgical Stapler," filed on Aug. 16, 2021, published as U.S. Pub. No. 2023/0051222 on Feb. 16, 2023; U.S. patent application Ser. No. 17/402,738, entitled "Firing Member Tracking Feature for Surgical Stapler," filed on Aug. 16, 2021, published as U.S. Pub. No. 2023/0049736 on Feb. 16, 2023; U.S. patent application Ser. No. 17/402,744, entitled "Adjustable Power Transmission Mechanism for Powered Surgical Stapler," filed on Aug. 16, 2021, published as U.S. Pub. No. 2023/0051938 on Feb. 16, 2023; U.S. patent application Ser. No. 17/402,749, entitled "Firing Bailout System for Powered Surgical Stapler," filed on Aug. 16, 2021, published as U.S Pub. No. 2023/0045998 on Feb. 16, 2023; and/or U.S. patent application Ser. No. 17/402,759, entitled "Deflectable Firing Member for Surgical Stapler," filed on Aug. 16, 2021, published as U.S. Pub. No. 2023/0052307 on Feb. 16, 2023. The disclosure of each of these applications is incorporated by reference herein in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a body;
   (b) a shaft assembly extending distally from the body;
   (c) an end effector disposed on a distal end of the shaft assembly, wherein the end effector includes a first jaw and a second jaw;
   (d) a stapling assembly supported by one of the first jaw or the second jaw of the end effector, wherein the stapling assembly includes a stapling assembly body and a wedge sled, wherein the wedge sled is configured to move relative to the stapling assembly body through a firing stroke to drive movement of a plurality of staples; and
   (e) a restriction feature, wherein the restriction feature is longitudinally fixed relative to the stapling assembly body throughout an entirety of the firing stroke and is configured to releasably hold the wedge sled in a predetermined position within the stapling assembly while the stapling assembly is in a pre-fired configuration, wherein at least a portion of the restriction feature is configured to respond to movement of the wedge sled to release the restriction feature from the wedge sled.

2. The surgical instrument of claim 1, wherein the stapling assembly comprises a staple cartridge configured to be received by the one of the first jaw or the second jaw, wherein the staple cartridge includes a cartridge body and a pan coupled to a portion of the cartridge body, wherein the pan includes one or more retainers defining the restriction feature.

3. The surgical instrument of claim 2, wherein the pan includes a pan body extending along a first axis parallel to a longitudinal axis defined by the cartridge body, wherein the one or more retainers extend along a second axis oriented at an angle relative to the first axis.

4. The surgical instrument of claim 2, wherein the one or more retainers are configured to bend relative to a portion of the pan.

5. The surgical instrument of claim 2, wherein the one or more retainers are integral with at least a portion of the pan.

6. The surgical instrument of claim 1, wherein the restriction feature is configured to move relative to at least a portion of the stapling assembly body to selectively engage and disengage the wedge sled.

7. The surgical instrument of claim 6, wherein the restriction feature includes an actuation portion and a lock portion opposite the actuation portion, wherein the lock portion is configured to engage the wedge sled.

8. The surgical instrument of claim 7, wherein the actuation portion includes a ramp, wherein the ramp is configured to engage at least a portion of the first jaw or the second jaw to drive movement of the lock portion relative to the wedge sled.

9. The surgical instrument of claim 7, wherein a portion of the stapling assembly defines an upper deck, wherein the actuation portion of the restriction feature protrudes from a portion of the upper deck.

10. The surgical instrument of claim 7, wherein the actuation portion is configured to respond to movement of the first jaw relative to the second jaw to drive movement of the lock portion relative to the wedge sled.

11. The surgical instrument of claim 7, wherein the stapling assembly includes a staple cartridge, wherein the staple cartridge is configured to be received in the first jaw, wherein the second jaw includes a support member, wherein movement of the first jaw relative to the second jaw is configured to actuate the actuation portion of the restriction feature via the support member while the staple cartridge is received within the first jaw.

12. The surgical instrument of claim 7, wherein the restriction feature defines a notch disposed between the actuation portion and the lock portion, wherein the notch is configured to receive at least a portion of the wedge sled.

13. The surgical instrument of claim 7, further comprising a pusher member in communication with a robotic arm, wherein the pusher member is configured to drive the wedge sled distally, wherein the pusher member is configured to engage the actuation portion of the restriction member to drive the restriction member laterally and thereby permit distal movement of the wedge sled.

14. The surgical instrument of claim 6, wherein at least a portion of the stapling assembly defines a proximal channel, wherein the restriction feature is configured to be received within the proximal channel.

15. The surgical instrument of claim 14, further comprising one or more detent features associated with the proximal channel or the restriction feature, wherein the detent features are configured to releasably hold the restriction feature in a predetermined position.

16. A surgical instrument, comprising:
(a) a body;
(b) a shaft extending distally from the body;
(c) an end effector operatively coupled with the shaft, wherein the end effector includes a first jaw and a second jaw;
(d) a stapling assembly associated with the first jaw or the second jaw of the end effector, wherein the stapling assembly includes a body defining a guard and a wedge sled, wherein the wedge sled is configured to move relative to the body of the stapling assembly from a pre-fired position to a fired position to drive movement of one or more staples in a stapling direction; and
(e) a restriction projection configured to engage the wedge sled to releasably hold the wedge sled in a predetermined position proximate a blade while the wedge sled is in the pre-fired position, wherein the restriction projection includes an actuation portion and a lock portion, wherein the actuation portion is configured to translate linearly in the stapling direction to thereby release the lock portion from a portion of the wedge sled.

17. The surgical instrument of claim 16, wherein at least a portion of the actuation portion extends through an opening defined by the body of the stapling assembly, wherein the lock portion is disposed within an interior of the body of the stapling assembly.

18. The surgical instrument of claim 16, wherein the restriction projection is movable between a locked position and an unlocked position, wherein the restriction projection is biased towards the locked position.

19. The surgical instrument of claim 16, wherein the actuation portion is translatable relative to the body of the stapling assembly to thereby release the lock portion from the wedge sled.

20. A method for use of a surgical instrument, the method comprising:
(a) receiving a staple cartridge into an end effector of the surgical instrument;
(b) restricting movement of a wedge sled of the staple cartridge during receipt of the staple cartridge into the end effector with a restriction projection that blocks distal movement of the wedge sled relative to a body of the staple cartridge, wherein the restriction projection remains longitudinally fixed relative to the body throughout the entirety of a firing stroke on the staple cartridge; and
(c) releasing movement of the wedge sled by moving at least a portion of the restriction feature relative to the wedge sled in response to movement of the wedge sled.

* * * * *